(12) United States Patent
Ruan et al.

(10) Patent No.: US 11,448,496 B2
(45) Date of Patent: Sep. 20, 2022

(54) NON-INVASIVE OPTICAL DETECTION SYSTEM AND METHOD USING PARTIALLY BALANCED INTERFEROMETRIC PARALLEL DETECTION

(71) Applicant: HI LLC, Los Angeles, CA (US)

(72) Inventors: Haowen Ruan, Los Angeles, CA (US); Hooman Mohseni, Santa Monica, CA (US)

(73) Assignee: HI LLC, Los Angeles, CA (US)

( * ) Notice: Subject to any disclaimer, the term of this patent is extended or adjusted under 35 U.S.C. 154(b) by 340 days.

(21) Appl. No.: 16/842,523

(22) Filed: Apr. 7, 2020

(65) Prior Publication Data

US 2020/0333130 A1 Oct. 22, 2020

Related U.S. Application Data

(60) Provisional application No. 62/855,405, filed on May 31, 2019, provisional application No. 62/834,505, filed on Apr. 16, 2019.

(51) Int. Cl.
 *A61B 5/05* (2021.01)
 *G01B 9/02091* (2022.01)
 (Continued)

(52) U.S. Cl.
 CPC ........ *G01B 9/02091* (2013.01); *A61B 5/0073* (2013.01); *G01B 9/02028* (2013.01); *G01N 21/4795* (2013.01)

(58) Field of Classification Search
 CPC ............ G01B 9/02091; G01B 9/02027; G01B 9/02028; G01B 9/02081; G01B 9/02087;
 (Continued)

(56) References Cited

U.S. PATENT DOCUMENTS 7,519,246 B2 4/2009 Welch et al.
8,654,320 B2 2/2014 Hasegawa et al.
(Continued)

FOREIGN PATENT DOCUMENTS

JP 2007114160 5/2007
WO WO2015109005 7/2015

OTHER PUBLICATIONS

Dawid Borycki, Oybek Kholiqov, and Vivek J. Srinivasan, "Reflectance-mode interferometric near-infrared spectroscopy quantifies brain absorption, scattering, and blood flow index in vivo," Opt. Lett. 42, 591-594 (Year: 2017).*

(Continued)

*Primary Examiner* — Tarifur R Chowdhury
*Assistant Examiner* — Jonathon Cook
(74) *Attorney, Agent, or Firm* — Michael J. Bolan; Vista IP Law Group, LLP

(57) ABSTRACT

Source light having a range of optical wavelengths is generated. The source light is split into sample light and reference light. The sample light is delivered into a sample, such that the sample light is scattered by the sample, resulting in signal light that exits the sample. The signal light and the reference light are combined into an interference light pattern having optical modes, each having a direct current (DC) component and at least one alternating current (AC) component. Different subsets of the optical modes of the interference light pattern are respectively detected, and analog signals representative of the optical modes of the interference light pattern are output. Pair of the analog signals are subtracted from each other, and differential analog signals are output. The sample is analyzed based on the differential analog signals.

20 Claims, 15 Drawing Sheets

(51) Int. Cl.
  *G01N 21/47* (2006.01)
  *A61B 5/00* (2006.01)
  *G01B 9/02015* (2022.01)
(58) Field of Classification Search
  CPC ............ G01B 9/02094; G01B 2290/45; A61B 5/0073; A61B 5/0042; G01N 21/4795
  See application file for complete search history.

(56) References Cited

U.S. PATENT DOCUMENTS

| | | | |
|---|---|---|---|
| 9,946,344 B2 | 4/2018 | Ayaz et al. | |
| 10,371,614 B2 | 8/2019 | Hosoda et al. | |
| 2006/0244973 A1* | 11/2006 | Yun | H01S 5/14 356/511 |
| 2016/0345880 A1 | 12/2016 | Nakaji et al. | |
| 2017/0227445 A1 | 8/2017 | Nakaji | |
| 2018/0249911 A1 | 9/2018 | Hosoda et al. | |

OTHER PUBLICATIONS

Dominik Wyser, et al., "Wearable and modular functional near-infrared spectroscopy instrument with multidistance measurements at four wavelengths", Neurophotonics, vol. 4, No. 04, Aug. 18, 2017, p. 1, XP055618655.
Hubin Zhao, et al., "Review of recent progress toward a fiberless, whole-scalp diffuse optical tomography system", Neurophotonics, vol. 5, No. 01, Sep. 26, 2017, p. 1, XP055619174.
Yanlu Li et al: "On-chip laser Doppler vibrometer for arterial pulse wave velocity measurement", Biomedical Optics Express, vol. 4, No. 7, Jun. 27, 2013 (Jun. 27, 2013), p. 1229, XP055619911.
Soren Aasmul et al: "Towards a compact multi-laser-beam device for cardiovascular screening", Retrieved from the Internet; Apr. 1, 2017 (Apr. 1, 2017), XP055619237; XP055619908.
Leteris Gounaridis et al: "Design of grating couplers and MMI couplers on the TriPleX platform enabling ultra-compact photonic-based biosensors", Sensors and Actuators B: Chemical, vol. 209, Mar. 1, 2015 (Mar. 1, 2015), pp. 1057-1063, XP055619192.
Zhao Wang et al: "Silicon photonic integrated circuit swept-source optical coherence tomography receiver with dual polarization, dual balanced, in-phase and quadrature detection", Biomedical Optics Express, vol. 6, No. 7, Jun. 17, 2015 (Jun. 17, 2015), p. 2562, XP055620031.
C. Weimann et al: "Silicon photonic integrated circuit for fast and precise dual-comb distance metrology", Optics Express, vol. 25, No. 24, Nov. 16, 2017 (Nov. 16, 2017), p. 30091, XP055619005.
Artundo Inigo: "Photonic Integration : New Applications Are Visible", Mar. 1, 2017 (Mar. 1, 2017), XP055619204.
Wim Bogaerts: "Introduction to Silicon Photonics Circuit Design", Mar. 11, 2018 (Mar. 11, 2018), XP055617994.
Joost Brouckaert et al: "Integration of Photodetectors on Silicon Photonic Integrated Circuits (PICs) for Spectroscopic Applications", Oct. 25, 2010 (Oct. 25, 2010), XP055617942.
Marc Korczykowski, "Perfusion functional MRI reveals cerebral blood flow pattern under psychological stress", Departments of Radiology, Neurology, Psychiatry, and Psychology and Center for Functional Neuroimaging , University of Pennsylvania, Philadelphia, PA 19104; pp. 17804-17809, PNAS, Dec. 6, 2005, vol. 102, No. 49.
D. Borycki et al., "Interferometric Near-Infrared Spectroscopy (iNIRS) for determination of optical and dynamical properties of turbid media," Opt. Express 24 (2016).
M. A. Choma et al., "Sensitivity advantage of swept source and Fourier domain optical coherence tomography," Opt. Express 11 (2003).
Z. Cheng et al., "On-chip photonic synapse," Sci. Advances 3, e1700160 (2017).
Z. Wang et al., "Silicon photonic integrated circuit swept-source optical coherence tomography receiver with dual polarization, dual balanced, in-phase and quadrature detection," Biomed. Opt. Express 6 (2015).
D. Vermeulen, S. Selvaraja, P. Verheyen, G. Lepage, W. Bogaerts, P. Absil, D. Van Thourhout, and G. Roelkens, "High-efficiency fiber-to-chip grating couplers realized using an advanced CMOS-compatible silicon on-insulator platform," Opt. Express 18(17), 18278-18283 (2010).
C. Li et al., "Compact polarization beam splitter for silicon photonic integrated circuits with a 340-nm-thick silicon core layer", Opt. Letters (2017).
L. Chen, C. R. Doerr, L. Buhl, Y. Baeyens, and R. A. Aroca, "Monolithically integrated 40-wavelength demultiplexer and photodetector array on silicon," IEEE Photon. Technol. Lett. 23(13), 869-871 (2011).
C. T. Santis et al., "High coherence semiconductor lasers based on integral high-Q resonators in hybrid Si/III-V platforms," PNAS 111 (2014).
Gratton G., Fabiani M., "Fast-optical Imaging of Human Brain Function," Frontiers in Human Neuroscience, vol. 4, Article 52, pp. 1-9, Jun. 2010.
Eggegracht A. T., et al., "Mapping Distributed Brain Function and Networks with Diffuse Optical Tomography," Nature Photonics 8 (2014)).
Hill D.K. and Keynes, R.D, "Opacity Changes in Stimulated Nerve," J. Physiol., vol. 108, pp. 278-281 (1949).
Foust A.J. and Rector D.M., "Optically Teasing Apart Neural Swelling and Depolarization," Neuroscience, vol. 145, pp. 887-899 (2007)).
Scott A. Diddams, et al., "Molecular fingerprinting with the resolved modes of a femtosecond laser frequency comb", Nature Letters, vol. 445 Feb. 8, 2007.
Shijun Xiao and Andrew M. Weiner, "2-D wavelength demultiplexer with potential for ≥ 1000 channels in the C-band", Optics Express, Jun. 28, 2004, vol. 12, No. 13.
M. Shirasaki, "Large angular dispersion by a virtually imaged phased array and its application to a wavelength demultiplexer", Optics Letters, vol. 21, No. 5, Mar. 1, 1996.
Kevin K. Tsia, "Simultaneous mechanical-scan-free confocal microscopy and laser microsurgery", Optics Letters, Jul. 15, 2009, vol. 34, No. 14.
S.R. Chinn and E.A. Swanson, "Optical coherence tomography using a frequency-tunable optical source", Optics Letters, Mar. 1, 1997, vol. 22, No. 5.
T. Bonin, G. Franke, M. Hagen-Eggert, P. Koch, and G. Hullmann, "In vivo Fourier-domain full-field OCT of the human retina with 15 million A-lines/s," Optics Letters, Oct. 15, 2010, vol. 35, No. 20.
J. Fujimoto and E. Swanson, "The Development, Commercialization, and Impact of Optical Coherence Tomography.," Invest. Ophthalmol. Vis. Sci. 57, Oct. 1-Oct. 13, 2016.
The Scientist and Engineer's Guide to Digital Signal Processing, "Chapter 9, Applications of the DFT", 16 pp.
Shoji Kishi, "Impact of swept cource optical coherence tomography on opthalmology", Department of Opthalmology, Gunma University Graduate School of Medicine, Maebashi, Japan, Sep. 29, 2015.
Wen Bao, et al., "Orthogonal dispersive spectral-domain optical coherence tomography", Optics Express, Apr. 21, 2014, vol. 22, No. 8.
PCT International Search Report and Written Opinion for International Appln. No. PCT/US2019/028881, Applicant Hi LLC, forms PCT/ISA/210, 220 and 237 dated Sep. 18, 2019 (23 pages).
Wenjun Zhou, et al., "Highly parallel, interferometric diffusing wave spectroscopy for monitoring cerebral blood flow dynamics", Optica, May 2018, vol. 5, No. 5 (10 pages).

\* cited by examiner

NON-INVASIVE OPTICAL DETECTION SYSTEM AND METHOD USING PARTIALLY BALANCED INTERFEROMETRIC PARALLEL DETECTION

RELATED APPLICATION DATA

Pursuant to 35 U.S.C. § 119(e), this application claims the benefit of U.S. Provisional Application Ser. No. 62/834,505, filed Apr. 16, 2019, and U.S. Provisional Application Ser. No. 62/855,405, filed May 31, 2019, which are expressly incorporated herein by reference.

FIELD OF THE INVENTION

The present inventions relate to methods and systems for non-invasive measurements in the human body, and in particular, methods and systems related to detecting a physiologically-dependent optical signal in the human body, e.g., the brain.

BACKGROUND OF THE INVENTION

Optical interferometry is a powerful tool to measure optical signals. As illustrated in FIG. 1, a typical optical interferometer 1 comprises an optical beam splitter 2 that splits a source light 3 into sample light 4 and a reference light 5. The sample light 4 interacts with a sample S and exits the sample as signal light 6 that carries optical information about the sample S, which can then be analyzed to determine certain characteristics about the sample S. Because signal light 6 is weak, e.g., lower than the noise floor of the optical detection, the reference light 5, which has a much higher light intensity, is used to interfere with the signal light 6 to boost the optical gain of the signal light 6.

To this end, the interferometer 1 further comprises an optical beam combiner 7 that combines the signal light 6 with the reference light 5 to produce interference light 8. The intensity of interference light 8 detected by a single optical detector can be given as:

$$I = I_S + I_R + 2\sqrt{I_S I_R} \cos(\Delta\omega t + \Delta\theta), \quad [1]$$

where $I_S$ is the intensity of the signal light 6, $I_R$ is the intensity of the reference light 5, $\Delta\omega$ is the frequency difference between the signal light 6 and reference light 5, $\Delta\theta$ is the phase difference between the signal light 6 and the reference light 5, and t denotes time. Since the reference light intensity $I_R$ is much higher than the signal light intensity $I_S$, the first term in equation [1] can be ignored. The second term in equation [1] can be considered a direct current (DC) offset that does not carry any information about the sample S. The third term in equation [1] is the alternating current (AC) interference term from which the information-carrying signal light 6 can be extracted and measured, and thus, carries information about the sample S, and is therefore, of particular interest.

Since the second term of equation [1] (i.e., the reference light intensity $I_R$) is very large, the dynamic range of the interference light 8 is very high, which poses a great challenge to conventional photodetectors. Moreover, even a small fluctuation of this strong reference light intensity $I_R$, e.g., such as that introduced by imperfections in the optical source (laser) that generates the source light 3, may generate a significant amount of noise as compared to the information-carrying signal of the AC interference term. Thus, it is critical to suppress this DC offset and its associated fluctuation. Although a low-pass filter could be used at the output of the interferometer 1 to attempt to suppress the DC offset, the fluctuations in the DC offset may generate frequencies (as noise) that coincide with the frequencies of the information-carrying AC interference term, which frequencies cannot be suppressed.

To address this challenge, the optical interferometer 1 utilizes full balanced detection to suppress the DC offset of the interference light 8. To achieve balanced detection, the optical interferometer 1 utilizes the interference light 8a, 8b from two ports of the optical beam combiner 7 and a matched pair of single optical detectors 9a, 9b that respectively detect the intensities of the interference light 8a, 8b. The optical properties of the optical beam combiner 7 are such that the interference light 8a output from one port of the optical beam combiner 7 and the interference light 8b output from the other port of the optical beam combiner 7 are 180° out-of-phase relative to each other.

In this case, the intensity of the interference light 8a can be given by:

$$I_A = I_S + I_R + 2\sqrt{I_S I_R} \cos(\Delta\omega t + \Delta\theta), \quad [2]$$

whereas the intensity of the interference light 8b can be given as:

$$I_B = I_S + I_R + 2\sqrt{I_S I_R} \cos(\Delta\theta t + \Delta\theta + \pi) = I_S + I_R - 2\sqrt{I_S I_R} \cos(\Delta\omega t + \Delta\theta) \quad [3]$$

In this case, the AC interference term in equation [3] is an inverted copy of the AC interference term in equation [2], while the first two terms in equation [3] are identical to the first two terms in equation [2].

The fully balanced detection setup of the optical interferometer 1 measures the intensities of the interference light 8a, 8b from both output ports of the optical beam combiner 7 using the detectors 9a, 9b. The difference between the measured intensities of the interference light 8a, 8b can then be subsequently computed, thereby cancelling out the small signal term (first term) and the large DC term (second term), and doubling the AC interference term (third term) in accordance with the equation:

$$I_A - I_B = 4\sqrt{I_S I_R} \cos(\Delta\omega t + \Delta\theta). \quad [4]$$

Thus, by measuring the difference between the intensities of the interference light 8a, 8b from two outputs of the optical beam combiner 7, the DC offset, including any of its frequency components caused by imperfections in the optical source, is significantly suppressed, while retaining the AC signals associated with the information-carrying signal light 6. The root mean square (RMS) of the differential signal in equation [4] is given by:

$$\text{RMS}(I_A - I_B) = 2\sqrt{2}\sqrt{I_S I_R}, \quad [5]$$

which is $\sqrt{2}$ higher than the RMS of the signal in equation [1] (i.e., the unbalanced detection setup).

Optical interferometry, with or without balanced detection, has been applied to the measurement of neural activity in the brain, which is useful for medical diagnostics, neuromodulation therapies, neuroengineering, or brain-computer interfacing. Conventional methods for measuring neural activity in the brain include diffusive optical imaging techniques, which employ moderate amounts of near-infrared or visible light radiation, thus being comparatively safe and gentle for a biological subject in comparison to X-Ray Computed Tomography (CT) scans, positron emission tomography (PET), or other methods that use higher-energy and potentially harmful ionizing radiation. Moreover, in contrast to other known methods, such as functional magnetic resonance imaging (fMRI), these optically-based imaging methods do not require large magnets or magnetic shielding, and thus, can be scaled to wearable or portable form factors, which is especially important in applications, such as brain-computer interfacing.

However, because optical imaging techniques rely on light, which scatters many times inside brain, skull, dura, pia, and skin tissues, the light paths occurring in these techniques comprise random or "diffusive" walks, and therefore, only limited spatial resolution can be obtained by a conventional optical detector, often on the order of centimeters, with usable penetration depths being limited to a few millimeters. The reason for this limited spatial resolution is that the paths of photons striking the detector in such schemes are highly variable and difficult, and even impossible, to predict without detailed microscopic knowledge of the scattering characteristics of the brain volume of interest, which is typically unavailable in practice (i.e., in the setting of non-invasive measurements through skull for detecting neural activity in the brain for brain-computer interfacing). In summary, light scattering has presented challenges for optical detection techniques in achieving high spatial resolution at deeper depths inside tissue. Moreover, the diffusive nature of light propagation also creates challenges for measurements of fast changes in optical scattering inside tissue, since essentially all paths between source and detector are highly scattered to begin with.

One commercially available non-invasive imaging method, referred to as optical coherence tomography (OCT), is capable of acquiring images with high z-resolution (depth) (see James Fujimoto, et al., "*The Development, Commercialization, and Impact of Optical Coherence Tomography*," Investigative Ophthalmology & Visual Science, Vol. 57, October 1-October 13 (2016). Traditional OCT systems use coherent light (typically light in the near-infrared spectrum) to capture sub-surface images within optical scattering media (such as biological tissue) at a micrometer-resolution. The OCT system enables optical imaging of samples in depth within a ballistic photon regime. In particular, the OCT system directs an optical beam at biological tissue and collects a small portion of the light that reflects from sub-surface features of the biological tissue. Although most of the light directed at the biological tissue is not reflected, but rather, diffusively scatters and contributes to background that may obscure the image, OCT utilizes a holographic (or interferometric) technique to select, via optical path selection, the photons that directly reflect off of the sub-surface features (i.e., the ballistic backscattered photons), and reject photons that scatter multiple times in the biological tissue before detection.

In particular, in a traditional OCT system, light from a light source is split into two paths along two different arms of an interferometer: a reference arm and a sample arm. In the sample arm, sample light is backscattered through a sample medium, and in the reference arm, reference light is back-reflected by a mirror where it recombines with the backscattered sample light at a coupler. An interference light pattern is formed by any sample light that has an optical pathlength that matches, within the coherence length of the optical source, the optical pathlength traveled by the reference light. The intensity of the backscattering sample light having that optical pathlength can then be detected within the interference light pattern.

Previous commercial OCT systems acquire data in the time domain (TD-OCT), and coherence gate the backscattered light from various depths in the biological tissue by adjusting the position of the mirror to tune the optical pathlength of the reference, such that only sample light having the matching optical pathlength is selected for detection at any given time. An alternative approach to coherence gating, referred to as Fourier domain optical coherence tomography (FD-OCT) is an imaging modality that does not involve adjusting the delay of the reference arm, but rather involves acquiring an interferometric signal as a function of optical wavelength by combining the sample light and the reference light from a source with a finite spectral width at a fixed reference arm delay, and then Fourier-transforming the spectral or frequency-resolved interference as a function of photon time-of-flight to obtain the various depths in the biological tissue. It has been shown that FD-OCT has a significantly greater signal-to-noise (SNR) than FD-OCT (see Michael A. Choma, et al., "*Sensitivity Advantage of Swept Source and Fourier Domain Optical Coherence Tomography*," Optics Express, Vol. 11, No. 18, 8 Sep. 2003).

Two distinct methods have been developed that employ the FD approach: (1) swept-source (SS-OCT), which time-encodes optical wavelengths by rapidly tuning a narrowband optical source through a broad optical bandwidth; and 2) spectral domain (SD-OCT), which uses a broadband light source to achieve spectral discrimination. Out of the OCT techniques, SS-OCT is the most closely related to the present inventions (see S. R. Chinn, et al., "*Optical Coherence Tomography Usinq a Frequency-Tunable Optical Source*," Optical Letter. Vo. 22, No. 5, pp. 340-342 (1997). SS-OCT has been reported to use a camera to measure the full-field OCT image (see Tim Bonin, et al., "*In Vivo Fourier-Domain Full-Field OCT of the Human Retina with 15 Million A-Lines/S*," Optics Letter, Vol. 35, No. 20, Oct. 15, 2010). However, the camera-based SS-OCT system described in Bonin lacks the necessary sensitivity and image quality.

Regardless of the type, the depth at which an OCT system images biological tissue is limited, because the quantity of ballistic photons decreases exponentially over depth. At greater depths the proportion of light that escapes without scattering (i.e., the ballistic light) is too small to be detected. Thus, the clinical applications of OCT have, thus far, been limited to imaging sub-surface features, such as obtaining high-resolution ophthalmic images of the retina. As such, OCT is presently insufficient for measuring neural activity in the deeper regions of the brain (i.e., deeper than 2 mm).

Another type of diffusive optical measurement technique, referred to as interferometric Near-Infrared Spectroscopy (iNIRS) (see Borycki, Dawid, et al., "*Interferometric Near-Infrared Spectroscopy (iNIRS) for Determination of Optical and Dynamical Properties of Turbid Media*," Optics Express, Vol. 24, No. 1, Jan. 11, 2016), has been developed. While traditional OCT utilizes low-coherence interferometry to produce cross-sectional images of biological specimens with a resolution of few micrometers and an imaging range of 1-2 mm, the goal of iNIRS is to use high coherence interferometry to measure optical and dynamical properties of thick scattering media at a depth on the order of a few centimeters at the cost of reduced resolution.

The current state of the art of iNIRS utilizes a single optical channel that measures the multiple-scattered photons from scattering samples, and therefore, has a limited data throughput, which leads to a lower SNR and detection speed. In response to the shortfalls of single-channel iNIRS systems, parallel iNIRS systems, which utilize multiple parallel channels to achieve parallel detection of the multi-scattered photons from scattering samples, have been developed thereby enabling higher data throughput, SNR, and detection speed. Such parallel iNIRS systems currently rely on commercially available high-speed cameras to detect the multi-scattered photons from the scattering samples.

The current state of the art of iNIRS utilizes a single optical channel that measures the multiple-scattered photons from scattering samples, and therefore, has a limited data throughput, which leads to a lower SNR and detection speed. In response to the shortfalls of single-channel iNIRS systems, parallel iNIRS systems, which utilize multiple parallel channels to achieve parallel detection of the multi-scattered photons from scattering samples, have been developed thereby enabling higher data throughput, SNR, and detection speed.

While balanced detection has been widely used in optical interferometric detection with single optical detectors that detect a single optical mode of the interference light, balanced detection is difficult to extend to parallel optical measurement systems, which would require a pair of optical detector arrays to measure multiple optical modes of the signal light in parallel. This challenge is due to the requirement that all of the optical modes of the interference light detected by the pair of detector arrays be 180° out-of-phase relative to each other. For example, with reference back to FIG. 1, the beam combiner 7 would have to be duplicated for each optical mode of the signal light to be detected. In the case where many optical modes must be measured (e.g., in the millions), it is very difficult to scale up an optical interferometric setup to detect these optical modes. As a result, conventional balanced detection has been limited to a single-channel optical interferometry, which has a limited performance in SNR and data throughput.

There, thus, remains a need for a more practical means of performing balanced detection in a multi-channel optical interferometric system.

SUMMARY OF THE INVENTION

In accordance with one aspect of the present inventions, a non-invasive optical detection system comprises an optical source configured for generating source light having a range of optical wavelengths during each of at least one measurement period. In one embodiment, the optical source is configured for sweeping the source light over the range of optical wavelengths during each of the measurement period (s).

The non-invasive optical detection system further comprises an interferometer configured for splitting the source light into sample light, which propagates along a sample arm of the interferometer, and reference light, which propagates along a reference arm of the interferometer, delivering the sample light into a sample, such that the sample light is scattered by the sample, resulting in signal light that exits the sample, and combining, during each of the measurement period(s), the signal light and the reference light into an interference light pattern having a plurality of optical modes, each having a direct current (DC) component and at least one alternating current (AC) component. In a preferred embodiment, each of the measurement period(s) is equal to or less than a speckle decorrelation time of the sample.

The non-invasive optical detection system further comprises an array of optical detectors configured for respectively detecting different subsets of the plurality of optical modes of the interference light pattern, and respectively outputting a plurality of high-bandwidth analog signals corresponding to the plurality of different subsets of optical modes of the interference light pattern. Each subset of optical modes of the interference light pattern may comprise a single optical mode or may comprise multiple spatially adjacent optical modes.

The non-invasive optical detection system further comprises differential analog circuitry configured for respectively subtracting pairs of the analog signals from each other, and respectively outputting a plurality of differential analog signals. In one embodiment, the non-invasive optical detection system further comprises the array of optical detectors and the differential analog circuitry. In another embodiment, each pair of analog signals corresponds to a pair of immediately neighboring ones of the plurality of optical detectors. In still another embodiment, each pair of analog signals corresponds to a respective pair of optical detectors that has a center-to-center spacing less than one millimeter, and preferably, less than one hundred microns. In yet another embodiment, subtracting the pairs of the analog signals from each other cancels at least a portion of the DC components in the respective pair of analog signals, such that the respective differential analog signal has a DC component that is less than ten percent (and preferably less than one percent) of the average of the DC components in the respective pair of analog signals.

The non-invasive optical detection system further comprises at least one processor configured for analyzing the sample based on the AC components of the plurality of differential analog signals. In one embodiment, the processor(s) is further configured for reducing the plurality of low-bandwidth digital signals to a single low-bandwidth digital signal, in which case, the processor(s) is configured for analyzing the sample based on the single low-bandwidth digital signal. In one embodiment, the sample is an anatomical structure, such that the signal light is physiologically is encoded with a physiologically-dependent optical signal in the anatomical structure, in which case, the processor(s) may be configured for identifying a change in the physiologically-dependent optical signal in the anatomical structure based on the plurality of low-bandwidth digital signals. The anatomical structure may be a brain, such that the physiologically-dependent optical signal (e.g., a fast-optical signal or a hemodynamic signal) is indicative of neural activity, in which case, the processor(s) may be configured for identifying neural activity in the brain based on the identified change in the physiologically-dependent optical signal.

In one embodiment, the source light has a range of optical wavelengths during each of the measurement period(s), such that at least one AC component of each optical mode of the interference light pattern comprises a plurality of oscillation frequency components respectively corresponding to a plurality of optical pathlengths extending through the sample. The optical source may be configured for sweeping the source light over the range of optical wavelengths during each of the measurement period(s). In this case, the processor(s) may be configured for analyzing the sample at a plurality of depths respectively corresponding to the plurality of optical pathlengths.

In an optional embodiment, the non-invasive optical detection system further comprises data compression circuitry configured for respectively compressing the plurality of differential analog signals, and respectively outputting a plurality of low-bandwidth digital signals, each having a frequency band less than a frequency band of the respective differential analog signal. In this case, the processor(s) is configured for analyzing the sample based on the plurality of low-bandwidth digital signals.

As one example, the data compression circuitry may comprise analog compression circuitry configured for parallel processing the plurality of differential analog signals, and respectively outputting the plurality of low-bandwidth digital signals. As another example, the data compression circuitry may comprise analog compression circuitry configured for parallel processing the plurality of differential analog signals, and respectively outputting a plurality of mid-bandwidth digital signals, each having a frequency band less than a frequency band of the respective differential analog signal. This data compression circuitry may further comprise digital compression circuitry configured for processing the plurality of mid-bandwidth digital signals over an N number of iterations, and respectively outputting the plurality of low-bandwidth digital signals on the Nth iteration, each low-bandwidth digital signal having a frequency band less than the frequency band of the respective mid-bandwidth digital signal.

In accordance with another aspect of the present inventions, a non-invasive optical detection method comprises generating source light having a range of optical wavelengths during each of at least one measurement period, splitting the source light into sample light and reference light, delivering the sample light into a sample, such that the sample light is scattered by the sample, resulting in signal light that exits the sample, and combining, during each of the measurement period(s), the signal light and the reference light into an interference light pattern having a plurality of optical modes with a first frequency band. In a preferred method, each of the measurement period(s) is equal to or less than a speckle decorrelation time of the sample.

The method further comprises respectively detecting different subsets of the plurality of optical modes of the interference light pattern, and respectively outputting a plurality of high-bandwidth analog signals corresponding to the different subsets of optical modes of the interference light pattern. Each subset of optical modes of the interference light pattern may comprises a single optical mode or may comprise multiple spatially adjacent optical modes.

The method further comprises respectively subtracting pairs of the analog signals from each other, and respectively outputting a plurality of differential analog signals. In one method, each pair of the analog signals corresponds to immediately neighboring ones of the plurality of optical modes of the interference light pattern. In another method, each pair of the analog signals corresponds to optical modes of the interference light pattern that are spaced from each other by less than one millimeter, and preferably less than one hundred microns. In still another method, respectively subtracting the pairs of the analog signals from each other cancels at least a portion of the DC components in the respective pair of analog signals, such that the respective differential analog signal has a DC component that is less than ten percent (and preferably less than one percent) of the average of the DC components in the respective pair of analog signals.

The method further comprises analyzing the sample based on the plurality of differential analog signals. One method further comprises reducing the plurality of low-bandwidth digital signals to a single low-bandwidth digital signal, in which case, the sample is analyzed based on the single low-bandwidth digital signal. In one method, the sample is an anatomical structure, such that the signal light is physiologically encoded with a physiologically-dependent optical signal in the anatomical structure, and the change in the physiologically-dependent optical signal in the anatomical structure is identified based on the plurality of low-bandwidth digital signals. The anatomical structure may be a brain, such that the physiologically-dependent optical signal (e.g., a fast-optical signal or a hemodynamic signal) is indicative of neural activity, in which case, neural activity in the brain may be identified based on the identified change in the physiologically-dependent optical signal.

In one method, the source light has a range of optical wavelengths during each of the measurement period(s), such that at least one AC component of each optical mode of the interference light pattern comprises a plurality of oscillation frequency components respectively corresponding to a plurality of optical pathlengths extending through the sample. For example, the method may further comprise sweeping source light over the range of optical wavelengths during each of the measurement period(s). In this case, the sample may be analyzed at a plurality of depths respectively corresponding to the plurality of optical pathlengths.

An optional method further comprises respectively compressing the plurality of differential analog signals, and respectively outputting a plurality of low-bandwidth digital signals, each having a frequency band less than a frequency band of the respective differential analog signal. In this case, the sample may be analyzed based on the plurality of low-bandwidth digital signals. In one example, respectively compressing the plurality of differential analog signals comprises parallel processing the plurality of differential analog signals, and respectively outputting the plurality of low-bandwidth digital signals. In another example, respectively compressing the plurality of differential analog signals comprises parallel processing the plurality of differential analog signals, and respectively outputting a plurality of mid-bandwidth digital signals, each having a frequency band less than a frequency band of the respective differential analog signal; and processing the plurality of mid-bandwidth digital signals over an N number of iterations, and respectively outputting the plurality of low-bandwidth digital signals on the Nth iteration, each low-bandwidth digital signal having a frequency band less than the frequency band of the respective mid-bandwidth digital signal.

In accordance with still another aspect of the present inventions, a multi-channel optical detector chip comprises an array of optical detectors configured for respectively detecting different subsets of the plurality of optical modes of a light pattern, each of the optical modes of the light pattern having a direct current (DC) component and at least one alternating current (AC) component. Each subset of optical modes of the interference light pattern may comprises a single optical mode or may comprise multiple spatially adjacent optical modes. The array of optical detectors is further configured for respectively outputting a plurality of analog signals representative of the plurality of optical modes of the interference light pattern; and The multi-channel optical detector chip further comprises differential analog circuitry configured for respectively subtracting pairs of the analog signals from each other, and respectively outputting a plurality of differential analog signals. In one embodiment, each pair of analog signals corresponds to a pair of immediately neighboring ones of the plurality of optical detectors. In another embodiment, each pair of analog signals corresponds to a respective pair of optical detectors that has a center-to-center spacing less than one millimeter, and preferably, less than one hundred microns. In still another embodiment, subtracting the pairs of the analog signals from each other cancels at least a portion of the DC components in the respective pair of analog signals, such that the respective differential analog signal has a DC component that is less than ten percent (and preferably less than one percent) of the average of the DC components in the respective pair of analog signals.

In an optional embodiment, the multi-channel optical detector chip further comprises data compression circuitry configured for respectively compressing the plurality of differential analog signals, and respectively outputting a plurality of low-bandwidth digital signals, each having a frequency band less than a frequency band of the respective differential analog signal.

As one example, the data compression circuitry may comprise analog compression circuitry configured for parallel processing the plurality of differential analog signals, and respectively outputting the plurality of low-bandwidth digital signals. As another example, the data compression circuitry may comprise analog compression circuitry configured for parallel processing the plurality of differential analog signals, and respectively outputting a plurality of mid-bandwidth digital signals, each having a frequency band less than a frequency band of the respective differential analog signal. This data compression circuitry may further comprise digital compression circuitry configured for processing the plurality of mid-bandwidth digital signals over an N number of iterations, and respectively outputting the plurality of low-bandwidth digital signals on the Nth iteration, each low-bandwidth digital signal having a frequency band less than the frequency band of the respective mid-bandwidth digital signal.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The embodiments of the non-invasive optical detection systems described herein are interferometric in that these optical detection systems mix detected signal light against reference light in order to increase the signal-to-noise ratio (SNR) of the signal light. These optical detection systems are described herein as, e.g., being Near-Infrared Spectroscopy (iNIRS) systems. This should be contrasted with conventional Optical Coherence Tomography (OCT) systems, which may utilize optical detector arrays in the form of camera pixels, but do so for a completely different purpose. That is, the non-invasive optical detection systems described herein focus on the measurement of multiple-scattered signal light of different depth-correlated optical pathlengths, as opposed to ballistic or single-scattered signal light measured by a conventional (OCT) system or a swept-source OCT (SS-OCT) system. Therefore, the non-invasive optical detection systems described herein are capable of detecting physiologically-dependent optical signals in tissue at a penetration depth of multiple centimeters.

Thus, the many camera pixels in the non-invasive optical detection systems described herein serve the purpose of increasing the SNR for such functional measurements within tissue at deeper depths, whereas known camera-based OCT approach, such as "full field OCT," utilizes an optical detector array to acquire actual images of the anatomical structure, and its use of many camera pixels, does not increase the SNR, but rather allows parallel imaging of many anatomical locations. Furthermore, unlike the non-invasive optical detection systems described herein, which provides for detection of multiple scattered light, the known camera-based OCT approach is not able to probe at deeper tissue depths because of its reliance on ballistic or single scattered light.

Notwithstanding the foregoing, it should be appreciated that the present inventions, in their broadest aspects, should not be limited to iNIRS systems, and may be embodied in any optical detection system that utilizes optical interferometry.

Significantly, unlike a conventional iNIRS system, which has a limited data throughput due to its single detector measurement of multi-scattered signal light, and thus has a lower signal-to-noise (SNR) and detection speed, the non-invasive optical detection systems described herein use an optical detector array to achieve parallel detection of the optical modes in the multiple-scattered signal light, thereby enabling higher data throughput, and thus a higher SNR and detection speed. The non-invasive optical detection systems described herein employ a unique partially-balanced optical detection technique that enables removal of the direct current (DC) component in all of the optical modes of detected physiologically-encoded signal light, thereby enabling balanced detection in multi-channel optical interferometry.

Figure 2:
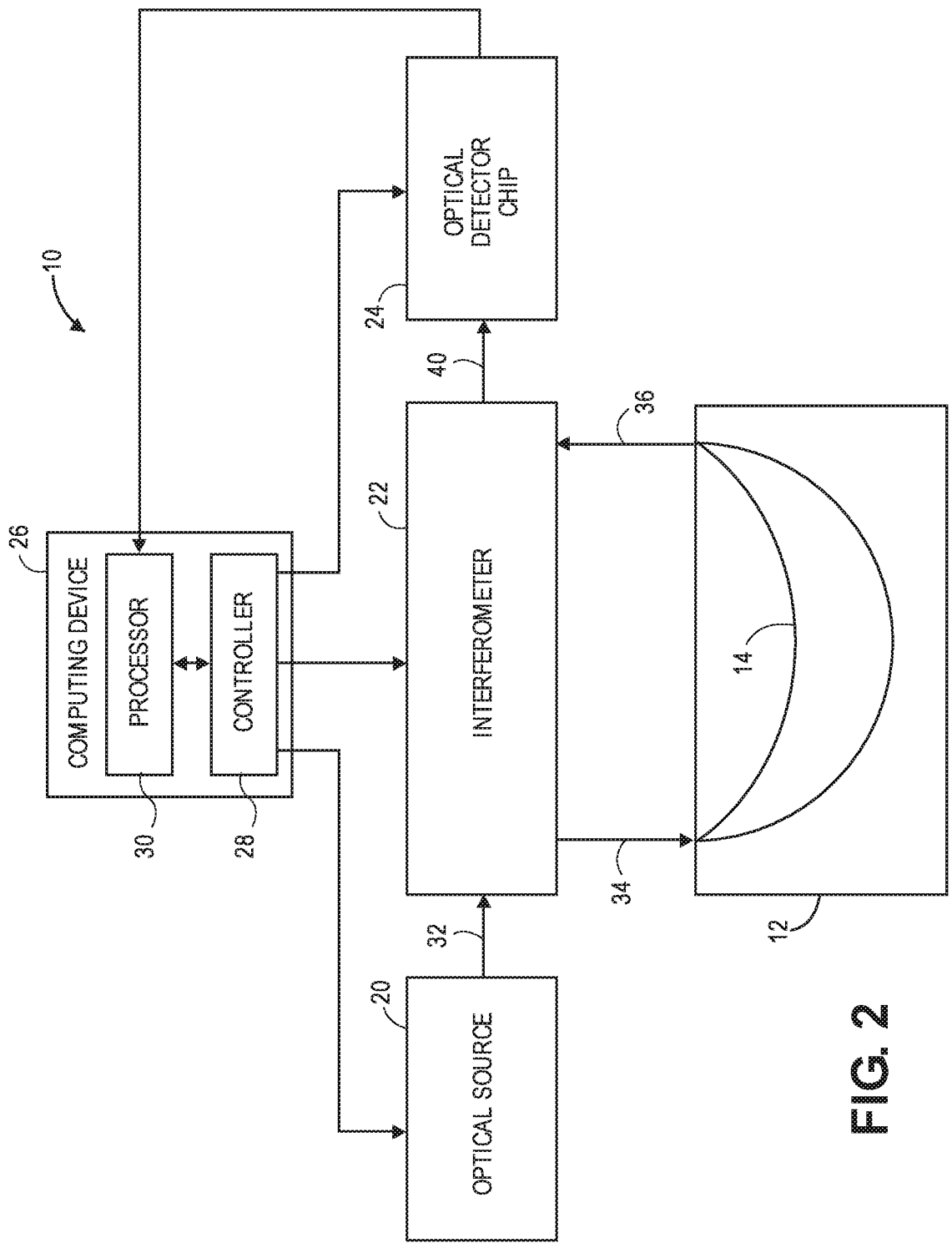
FIG. 2 is a block diagram of a non-invasive optical detection system constructed in accordance with one embodiment of the present inventions.

Referring now to FIG. 2, a generalized embodiment of an optical detection system 10 constructed in accordance with the present inventions will now be described. The non-invasive optical detection system 10 is configured for acquiring signal light in a sample 12, processing the signal light, and determining a characteristic of the sample 12 based on the processed signal light. In the illustrated embodiment, the sample 12 is an anatomical structure, and as such, the non-invasive optical detection system 10 is configured for non-invasively acquiring physiologically-encoded signal light (i.e., signal light representative of a physiologically-dependent optical signal) in the anatomical structure 12, processing the physiologically-encoded signal light, and determining the presence and depth of the physiologically-dependent optical signal in the anatomical structure 12 based on the processed physiologically-encoded signal light.

In the illustrated embodiments, the anatomical structure 12 is a brain, in which case, the non-invasive optical detection system 10 may be further configured for identifying the presence and location of neural activity within the brain 12 based on the physiologically-dependent optical signal. Although for exemplary purposes, the non-invasive optical detection system 10 is described as acquiring physiologically-encoded information from brain tissue, variations of such optical detection system 10 may be used to acquire physiologically-encoded information from other anatomical structures of a human body, animal body and/or biological tissue.

In the illustrated embodiments, the physiologically-dependent optical signal may be a fast-optical signal (i.e., perturbations in the optical properties of neural tissue caused by mechanisms related to the depolarization of neural tissue, including, but not limited to, cell swelling, cell volume change, changes in membrane potential, changes in membrane geometry, ion redistribution, birefringence changes, etc.), or the physiologically-dependent optical signal may be a slower hemodynamic change, e.g., Doppler shift due to moving blood flow, changes in blood volume, metabolism variations such a blood oxygen changes. However, as will be described in further detail below, the non-invasive optical detection system 10, when properly tuned to a specific type of physiologically-dependent optical signal, is capable of decoding light propagating through the brain to detect any signal that causes a change in an optical property of the brain 12.

The neural activity information (or the acquired physiologically-encoded information from which it is derived) may be transmitted to external programmable devices for use (e.g., computed, processed, stored, etc.) therein, e.g., medical devices, entertainment devices, neuromodulation stimulation devices, lie detection devices, alarm systems, educational games, brain interface devices, vehicle's audio systems, vehicle's autonomous driving systems, etc., and/or may be used internally to adjust the detection parameters of the non-invasive optical measurement system 10, such as increasing or decreasing the strength of the optical source and/or data compression and/or analysis, such a Fast Fourier Transform (FFT) and/or statistical analysis.

Although the non-invasive optical detection system 10, for purposes of brevity, is described herein as acquiring physiologically-encoded information from the brain 12 by using a single fixed source/detector-array pair arrangement to create one bundle of detected optical paths 14 through the brain 12 in a single measurement period, in a practical implementation capable of detecting and localizing the physiologically-dependent optical signal in an x-y plane along the surface of the brain 12, variations of the non-invasive optical detection system 10 may utilize more complex source-detector arrangements (e.g., single-source multi-detector, multi-source single-detector, or multi-source multi-detector) to simultaneously create multiple optical path bundles 14 spatially separated from each other within the brain 12 in a single measurement period, or may utilize a movable source-detector arrangement to sequentially create multiple optical path bundles 14 over several measurement periods, as described in U.S. Provisional Patent Application Ser. No. 62/692,074, entitled "Frequency Domain Optical Spectroscopy For Neural Decoding," and U.S. Provisional Patent Application Ser. No. 62/692,124, entitled "Interferometric Frequency-Swept Source and Detector in a Photonic Integrated Circuit," which are expressly incorporated herein by reference. Thus, in a practical implementation, the non-invasive optical detection system 10 may detect and localize physiologically-dependent optical signals associated with neural activity in the brain, including fast-optical signals, in three-dimensions, with two of the dimensions represented as an x-y plane spanning the surface of the brain 12 encoded within the spatially separated multiple sample paths and the third dimension (z-dimension or depth into the brain 12) being encoded within frequency components of photons propagating along the sample paths.

Referring still to FIG. 2, the non-invasive optical detection system 10 generally comprises an optical source 20, an interferometer 22, at least one multi-channel optical detector chip 24 (only one is shown in FIG. 2, although several may be used in a typical embodiment, e.g., in a complex source-detector arrangement), and a computing device or other similar device 26, which all operate together to non-invasively detect the presence and depth of a physiologically-dependent optical signal in the brain 12.

The computing device 26 comprises a controller 28, a processor 30, a memory (not shown), a display (not shown), and an input device (not shown). The computing device 26 can, e.g., be a computer, tablet, mobile device, or any other suitable device for processing information. The computing device 26 can be local to the user or can include components that are non-local to the user. For example, in at least some embodiments, the user may operate a terminal that is connected to a non-local computing device. In other embodiments, the memory can be non-local to the user. The computing device 26 can utilize any suitable processor 30, including one or more hardware processors that may be local to the user or non-local to the user or other components of the computing device 26. The processor 30 is configured to execute instructions provided to the processor 30, as described below.

Any suitable memory can be used for the computing device 26. The memory can be a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal. The term "modulated data signal" can include a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display can be any suitable display device, such as a monitor, screen, or the like, and can include a printer. In some embodiments, the display is optional. In some embodiments, the display may be integrated into a single unit with the computing device 26, such as a tablet, smart phone, or smart watch. The input device can be, for example, a keyboard, mouse, touch screen, track ball, joystick, voice recognition system, or any combination thereof, or the like.

Although the controller 28 and processor 30 are described herein as being separate components, it should be appreciated that portions or all functionality of the controller 28 and processor 30 may be performed by a single component. Furthermore, although all of the functionality of the controller 28 is described herein as being performed by a single component, and likewise all of the functionality of the processor 30 is described herein as being performed by a single component, such functionality each of the controller 28 and the processor 30 may be distributed amongst several components. It should also be appreciated that all or a portion of the controller 28 may be located outside of a physical computing device, e.g., as a Field Programmable Gate Array (FPGA). Moreover, it should be appreciated that those skilled in the art are familiar with the terms "controller" and "processor," and that they may be implemented in software, firmware, hardware, or any suitable combination thereof.

The optical source 20 may take the form of a distributed feedback (DFB) laser, although other light sources, e.g., highly coherent vertical cavity surface emitting laser (VC-SEL), distributed Bragg reflector (DBR) laser, a Fourier domain mode locked (FDML) laser, a super luminescent diode (SLD), a light emitting diode (LED), a diode-pumped solid-state (DPSS) laser, a laser diode (LD), a titanium sapphire laser, a micro light emitting diode (mLED), or similar laser to achieve very narrow spectral linewidths and extremely high amplitude stability, among other optical sources, may be used.

The optical source 20 may have either a predefined coherence length or a variable coherence length. Since the goal of the non-invasive optical detection system 10 is to measure optical and dynamic properties at deeper depths within brain tissue, as opposed to acquiring images of the brain tissue at a shallow depths by using conventional OCT systems, the optical source 20 preferably has an instantaneous spectral linewidth and tuning range narrower by several orders of magnitude than in typical OCT systems, enabling the measurement of distinctly longer optical pathlengths (of up to tens of centimeters) at the cost of reduced resolution (of the order of millimeters). Preferably, the optical source 30 has a coherence length of at least 5 cm, an instantaneous spectral linewidth of less than 2 nm, and preferably less than 0.5 nm, and a tuning range of the wavelength greater than 3 pm, and preferably greater than 30 pm.

The optical source 20 is configured for generating source light 32, which may, e.g., be ultraviolet (UV) light, visible light, and/or near-infrared and infrared light, and may have any suitable wavelength, e.g., in the range of 350 nm-1800 nm. The source light 32 may be close to monochromatic in nature, comprising approximately a single-wavelength light, or the source light 32 may have multiple wavelengths (e.g., white light). It is preferred that the optical wavelength of the source light 32 be selected to maximize sensitivity to the specific physiologically-dependent optical signal of interest. For example, in the case where the physiologically-dependent optical signal of interest is a fast-optical signal, an optical wavelength greater than hemoglobin absorption wavelengths (e.g., greater than 850 nm) may be used for the source light 32 to detect scattering changes by materials other than blood, and/or to detect scattering by blood outside of wavelengths that are strongly absorbed by blood. Optionally, an optical wavelength equal to or greater than 1000 nm may be used for the source light 32 to maximize penetration. In the case where the physiologically-dependent optical signal of interest is a hemodynamic optical signal (e.g., blood oxygen concentration), an optical wavelength in the range of 550 nm to 850 nm may be used for the source light 32. Multiple optical wavelengths can be used for the source light 32 to allow different physiologically-dependent optical signals to be distinguished from each other. For example, source light 32 having two optical wavelengths of 900 nm and 700 nm can be respectively used to resolve fast-optical signals and blood oxygenation. Alternatively, the wavelength of the source light 32 can be selected to maximize the sensitivity of the multi-channel optical detector chip 24.

The source light 32 generated by the optical source 20 has a range of optical wavelengths. In the illustrated embodiment, the source light 32 has a narrow optical spectrum, and the optical source 20, under control of the controller 28 (shown in FIG. 2), rapidly sweeps (or "chirps") the source light 32 over the range of optical wavelengths as a function of time to functionally mimic or create an effective broad optical spectrum. In this manner, depth information is encoded into the resulting signal light, as will be described in further detail below. Alternatively, instead of sweeping the source light 32, the optical source 20 may output source light 32 having a broad optical bandwidth of, e.g., 10 pm to 1 nm.

The optical source 20 may receive input current from a drive circuit (not shown), e.g., a laser diode current driver, that can be varied to sweep the source light 32 output by the optical source 20. As briefly discussed above, a DFB laser may be used for the optical source 20. The DFB laser comprises an optical cavity having a diffraction grating that serves as a wavelength selective element and provides optical feedback that reflects light back into the cavity to form the resonator. The grating is constructed so as to reflect only a narrowband of wavelengths, and thus produce a single longitudinal lasing mode. Altering the temperature of the DFB laser causes the pitch of the grating to change due to the dependence of refractive index on temperature, thereby altering the wavelength of the output, thereby making the DFB laser tunable on the order of 6 nm for a 50° K change in temperature. Altering the current powering the DFB laser causes a temperature change inside of the DFB laser, thereby allowing it to be tuned in a controlled manner. In one exemplary embodiment, the central wavelength of the DFB laser may be in the range of 600 nm-900 nm with a tunable frequency of 10 GHz and the frequency of the DFB laser may be swept at a repetition as small as 10 μs (i.e., a 100 KHz chirp repetition rate).

The sweep rate of the optical source 20 defines a measurement period of the non-invasive optical detection system 10 in accordance with the equation:

$$t = 1/R, \quad [6]$$

where t is the measurement period, and R is the uni-directional rate (forward sweep or reverse sweep).

Figure 3:
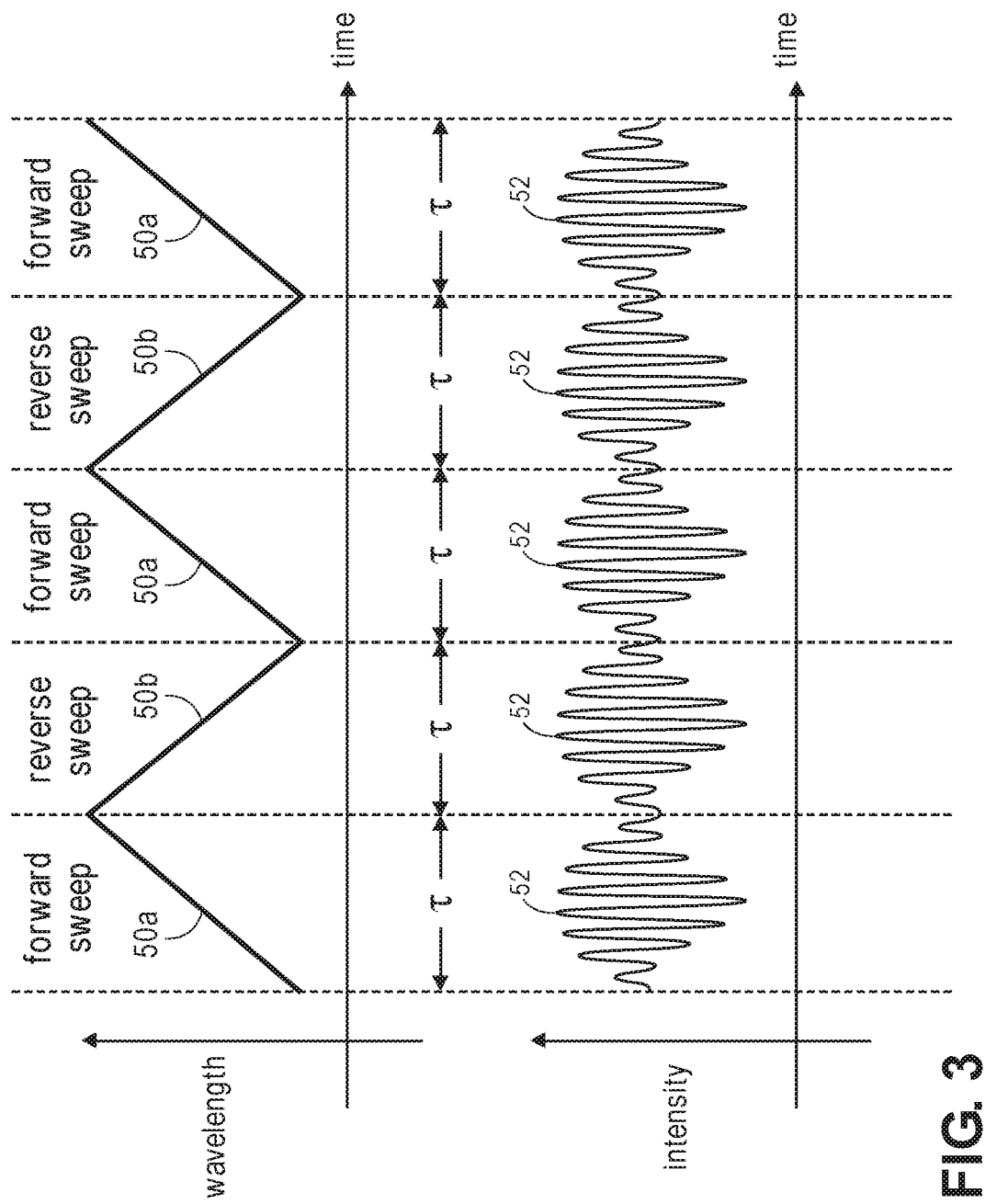
FIG. 3 is a timing diagram illustrating the optical sweeps performed by the non-invasive optical detection system of FIG. 1, and fringe patterns in interference light patterns resulting from the optical sweeps.

As illustrated in FIG. 3, the optical source 20 sweeps across a range of optical wavelengths during the measurement period t. In the illustrated embodiment, the measurement periods t are respectively defined by both forward sweeps 50a (low to high wavenumbers) and rearward sweeps 50b (high to low wave numbers) of the optical source 20, thereby maximizing the usage of the full sweep range of the optical source 20. However, in alternative embodiments, all of the measurement periods t are defined by either forward sweeps 50a or reverse sweeps 50b (but not both), such that there are idle time intervals between sequential measurement periods t equal to the time period of a unilateral sweep R. However, because the data throughput is generally limited by the detection and processing scheme, the existence of the idle time intervals between the measurement periods t will generally not limit the data throughput of the non-invasive optical detection system 10.

Notwithstanding this, the uni-directional sweep rate R of the optical source 20 may be any suitable rate, but preferably, defines a measurement period t that is no longer than the duration of the signal of interest, and furthermore, is no longer than the speckle decorrelation time (which is due to the scatterers' motion inside tissue, and rapidly decreases with the depth of the tissue, and in particular, scales super-linearly with the depth into tissue, falling to microseconds or below as the tissue depth extends to the multi-centimeter range) of brain tissue. For example, the measurement period t may be equal to or less than 100 μs (equivalent to a uni-directional sweep rate of 10 KHz), and preferably equal to or less than 10 μs (equivalent to a uni-directional sweep rate of 100 KHz).

The interferometer 22 is a Mach-Zehnder-type interferometer that is configured for splitting the source light 32 from the optical source 20 into sample light 34, which is delivered to the brain 12 along a sample arm and exits the brain 12 as physiologically-encoded signal light 36, and reference light 38 (shown in FIG. 4), which propagates along a reference arm outside of the brain 12. The interferometer 22 is further configured for combining the physiologically-encoded signal light 36 with the reference light 38 to create an interference light pattern 40 corresponding to the optical modes of the physiologically-encoded signal light 36, and an AC component, which contains oscillation frequency components corresponding to different optical pathlengths of the sample light 34 propagating through the brain 12, which in turn correspond to different depths in the brain 12. As will be described in further detail below, the interference light pattern 40 further comprises an undesirable direct current (DC) component contributed by the reference light 38. In the illustrated embodiment, the interference light pattern 40 takes the form of an interference light speckle pattern having a plurality of optical modes (or speckle grains).

Figure 4:
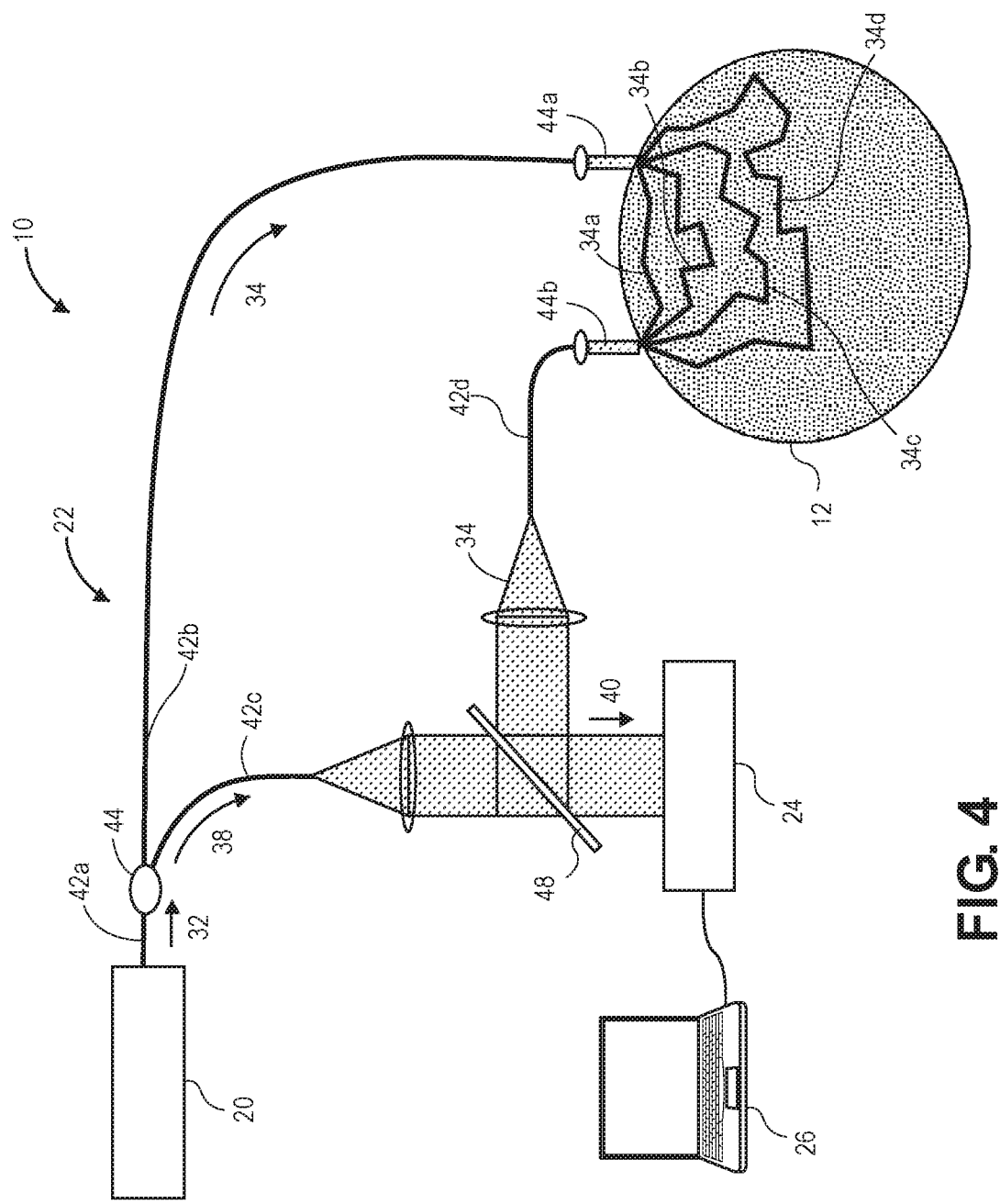
FIG. 4 is a plan view of one embodiment of an interferometer used in the non-invasive optical detection system of FIG. 1.

Referring to FIG. 4, a more detailed implementation of the interferometer 22 in the context of the non-invasive optical detection system 10 will now be described. In this implementation, the interferometer 22 is optical fiber-based (i.e., uses optical fibers to direct light between the components), although in alternative embodiments, the interferometer 22 may direct light via free-space propagation between the components using optics, such as mirrors, as further illustrated in U.S. patent application Ser. No. 16/266,818, entitled "Ultrasound Modulating Optical Tomography Using Reduced Laser Pulsed Duration," U.S. patent Ser. No. 16/299,067, entitled "Non-Invasive Optical Detection Systems and Methods in Highly Scattering Medium," and U.S. patent application Ser. No. 16/382,461, entitled "Non-Invasive Optical Detection System and Method," which are expressly incorporated herein by reference.

The interferometer 22 comprises an input optical fiber 42a that optically couples the interferometer 22 to the optical source 20 for receiving the source light 32 from the optical source 20. The interferometer 22 further comprises an optical fiber-based optical beam splitter 44 for splitting the source light 32 into the sample light 34 and the reference light 38. The optical beam splitter 44 may not necessarily split the source light 32 equally into the sample light 34 and the reference light 38, and it may actually be more beneficial for the optical beam splitter 44 to split the source light 32 unevenly, such that the intensity of the sample light 34 is less than the intensity of the reference light 38 (e.g., 99/1 power ratio), since much of the sample light 34 will be lost after passing through the head. That is, the intensity of the sample light 34 should be boosted relative to the reference light 38 to compensate for the losses incurred by the sample light 34 as it passes through the head and the fact that only a small portion of signal light (described below) exiting the head will be detected.

The interferometer 22 further comprises a sample arm optical fiber 42b and a reference arm optical fiber 42c for respectively propagating the sample light 34 and the reference light 38 along the sample arm and the reference arm of the interferometer 22. The sample arm optical fiber 42b delivers the sample light 34 via an output port 46a into the brain 12, such that the sample light 34 scatters diffusively through the brain 12, and back out again, exiting as the physiologically-encoded signal light 36. As the sample light 34 scatters diffusively through the brain 12, various portions 34a-34d of the sample light 34 will take different paths through the brain 12, which combine into the exiting physiologically-encoded signal light 36. For purposes of brevity, only four sample light portions 34a-34d are illustrated as traveling along optical paths of different lengths (from shallow to deep), which combined into the exiting neural-encoded signal light 36, although it should be appreciated that the diffused sample light 34 will travel along many more optical paths through the brain 12. As the sample light 34 interacts with the brain 12, multiple optical modes develop and appear in the physiologically-encoded signal light 36 as speckle grains.

The interferometer 22 further comprises an output optical fiber 42d configured for receiving the physiologically-encoded signal light 36 from the brain 12 via an input port 46b. To maintain the multiple optical modes of the physiologically-encoded signal light 36 received from the brain 12 via the input port 44b, the output optical fiber 40d is a multi-mode output optical fiber. The sample arm optical fiber 40b may also comprise a multi-mode optical fibers and/or single-mode optical fiber bundle, whereas the input optical fiber 40a and the reference arm optical fiber 40c are preferably single-mode optical fibers.

The interferometer 22 further comprises a single optical beam combiner 48 configured for receiving the physiologically-encoded signal light 36 from the output optical fiber 42d, receiving the reference light 38 from the reference arm optical fiber 42c, and combining the physiologically-encoded signal light 36 and the reference light 38 via superposition to generate the interference light pattern 40. In the illustrated embodiment, the optical beam combiner 48 is a free-space optical beam combiner that respectively receives the physiologically-encoded signal light 36 and the reference light 38 on different faces of the optical beam combiner 48 and outputs the interference light pattern 40 on another different face of the optical beam combiner 48. In this case, collimators (not shown) can be located between the optical beam combiner 48 and the output optical fiber 42d and reference arm optical fiber 42c to collimate the physiologically-encoded signal light 36 and the reference light 38 at the respective faces of the optical beam combiner 48.

As discussed above, the optical source 20, in the illustrated embodiment, sweeps the source light 32 over a range of optical wavelengths, such that depth information is encoded within the physiologically-encoded signal light 36. In effect, the resulting physiologically-encoded signal light 36 exiting the brain 12 will have a time-of-flight (TOF) profile encoded with different optical pathlengths L (or depths in the brain 12) in accordance with the equation: $L/Cn_r$, where c is the speed of light and $n_r$ is the refractive index of tissue).

Figure 5A:
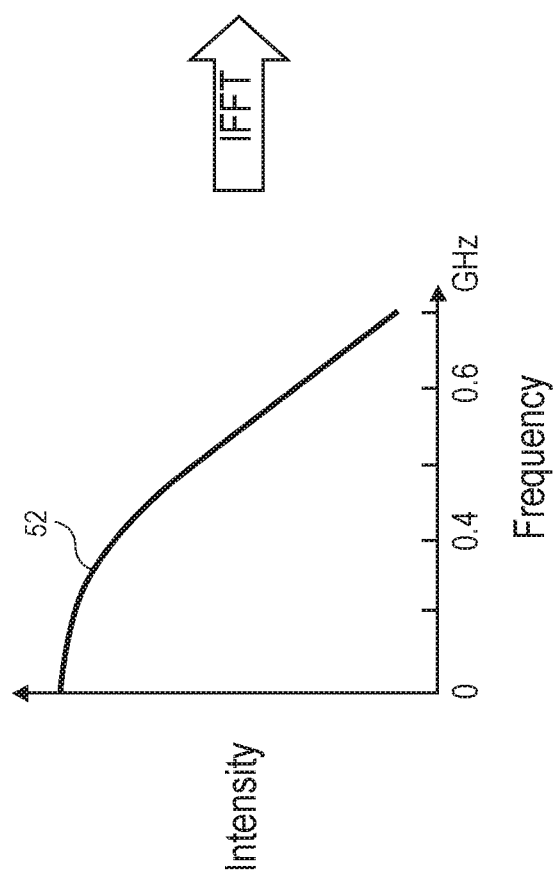
FIG. 5A is a diagram illustrating an exemplary frequency component-intensity profile detected by the non-invasive optical detection system of FIG. 2.
Figure 5B:
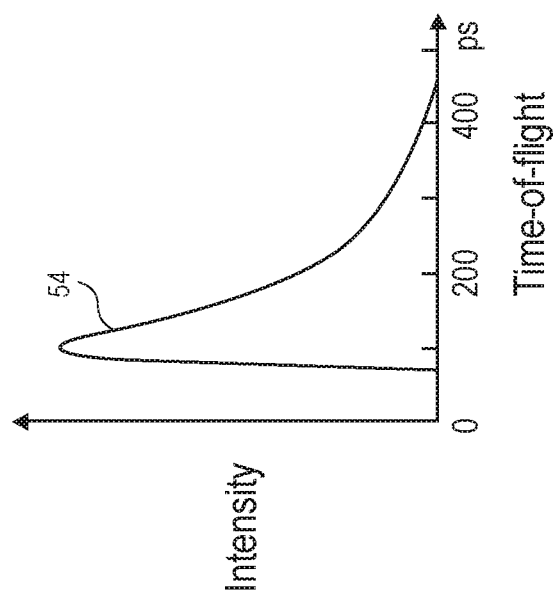
FIG. 5B is a diagram illustrating an exemplary time-of-flight (TOF)-intensity profile transformed from the frequency component-intensity profile of FIG. 5A.
Figure 6A:
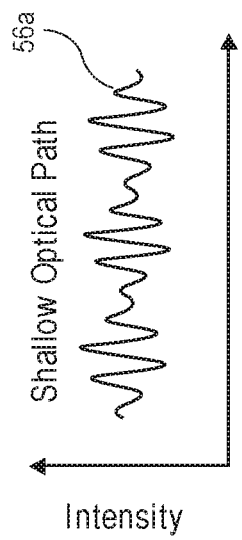
FIG. 6A is a timing diagram illustrating a series of fringe patterns of an interference light pattern corresponding to a shallow optical path.
Figure 6B:
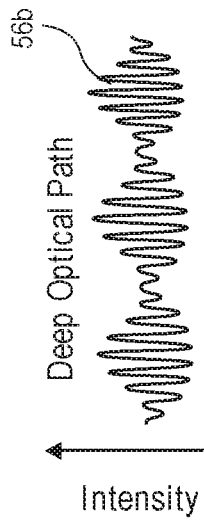
FIG. 6B is a timing diagram illustrating a series of fringe patterns of an interference light pattern corresponding to a deep optical path.
Figure 7A:
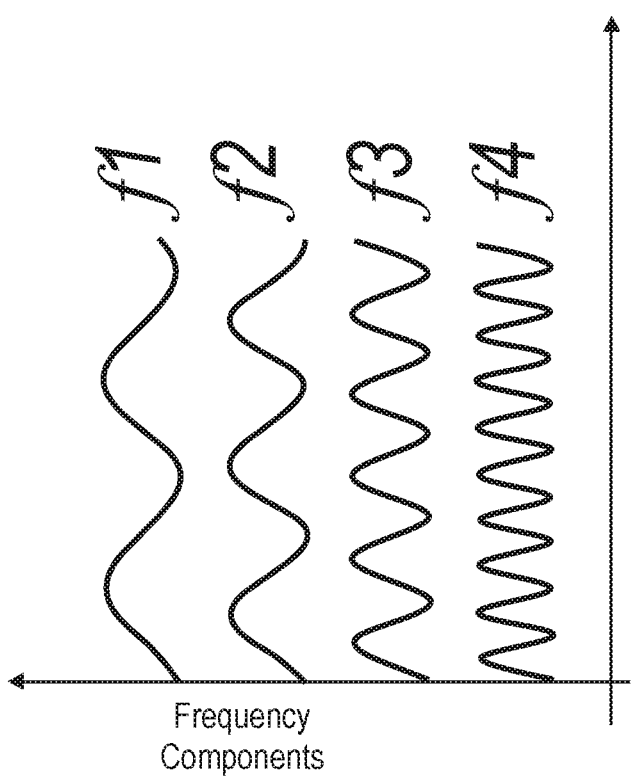
FIG. 7A is a timing diagram illustrating exemplary oscillation frequency components of an interference light pattern generated by the non-invasive optical detection system of FIG. 2.
Figure 7B:
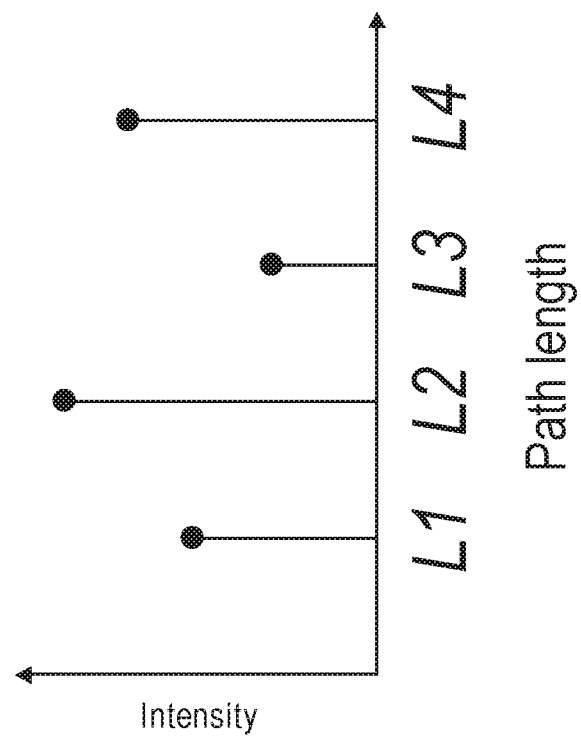
FIG. 7B is a timing diagram illustrating exemplary optical pathlength intensities corresponding to the exemplary oscillation frequency components of FIG. 7A.

In particular, as a result of sweeping the source light 32 over a range of optical wavelengths, the physiologically-encoded signal light 36 has a frequency component-intensity profile 52, as illustrated in FIG. 5A, which corresponds to a time-of-flight (TOF)-intensity profile 54, as illustrated in FIG. 5B. As shown in FIGS. 6A and 6B, this frequency component-intensity profile 52 comprising intensity values of the oscillation frequency components 56, which are encoded with optical pathlength information, and thus, different depths of the brain 12. It follows from this that a relatively shallow optical path will yield a relatively slow oscillation frequency component 56a (see FIG. 6A), whereas a relatively deep optical path will yield a relatively fast oscillation frequency component 56b (see FIG. 6B). As one example, four exemplary oscillation frequency components f1-f4 (see FIG. 7A) respectively correspond to four exemplary intensities of the light at four different optical pathlengths L1-L4 (see FIG. 7B) which directly correlate to depths of the physiologically-dependent optical signal within the brain 12).

The multi-channel optical detector chip 24 may be implemented as a camera with a frame rate that can be controlled by the controller 28 in coordination with the optical wavelength sweeps of the optical source 20 to match the measurement period t. Significantly, the multi-channel optical detector chip 24 is a compact, low-power chip that comprises a very large number (thousands to hundreds of thousands) of parallel independent channels. Each channel of the multi-channel optical detector chip 24 may monitor a pair of subsets of optical modes of the physiologically-encoded signal light 36 (i.e., speckle grain), thereby enabling many optical modes of the physiologically-encoded signal light 36 (i.e., many speckle grains) to be measured in parallel. In one embodiment, the multi-channel optical detector chip 24 is affixed directly to the face of the optical beam combiner 48 from which the interference light pattern 40 exits.

Figure 8:
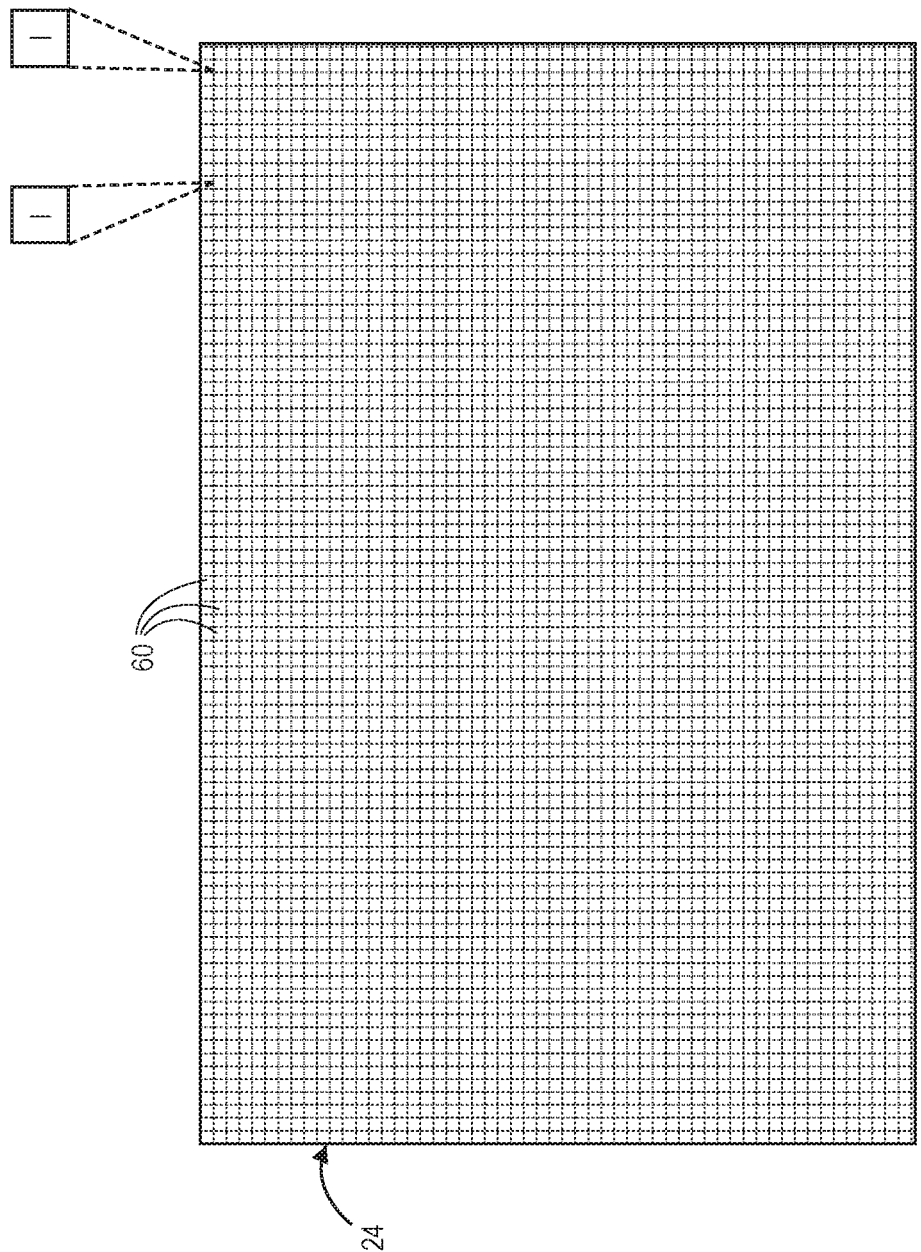
FIG. 8 is a plan view of an optical detector array used in the non-invasive optical detection system of FIG. 2.

As shown in FIG. 8, the multi-channel optical detector chip 24 comprises an array of optical detectors 60 (e.g., 100×100 pixels) configured for simultaneously detecting the different subsets of the optical modes of the interference light pattern 40, and outputting an array of intensity values I respectively of the different subsets of optical modes of the interference light pattern 40 during each measurement period t. In the case where the interference light pattern 40 is a speckle light pattern, the optical modes are speckle grains (approximately the size of a wavelength of the light) of the speckle light pattern 40. Due to the pairing of the optical modes sets, if the number of optical modes detected by the multi-channel optical detector chip 24 is N, and the number of optical modes of the interference light pattern 40 detected by a single optical detector 60 is M, the optical detector chip 24 will have an N/2M number of channels. The multi-channel optical detector chip 24 may be implemented using any suitable technology, e.g., CMOS technology. Each optical detector 60 is preferably very small, e.g., 100 μm×100 μm, thereby minimizing the size and power consumption of the multi-channel optical detector chip 24. The multi-channel optical detector chip 24 may have less than 100% fill-factor (e.g., 50% fill-factor), e.g., the optical detection region and the electronics may be in a side-by-side configuration for each pixel, or may have 100% fill-factor, e.g., the optical detection region and the electronics may be in a stacked configuration for each pixel.

It should be appreciated that having a multi-channel optical detector chip 24 has two significant advantages.

First, the use of a large number of independent channels detects the interference light pattern 40 derived from an area of the brain 12, as opposed to a single point of the brain 12, which increases the spatial resolution of the multi-channel optical detector chip 24, thereby allowing for better identification and classification of neural activity in the brain 12, and eventually a higher probability of detecting certain neural activity in the brain 12 with higher confidence.

Second, the overall sensitivity of the optical signal detection increases with the number of independent channels of the multi-channel optical detector chip 24 in accordance with $\sqrt{N}$, where N is the number of independent channels. Thus, the use of a large number of pixels 60 in the multi-channel optical detector chip 24 ultimately increases the SNR of the detected interference light pattern 40 relative to a conventional iNIRS system that uses a single large detector.

That is, in the case where a single detector was used in the conventional iNIRS system, the use of only one channel for detection, results in the averaging of all of the optical modes of the interference light pattern 40 during each measurement period t, and hence destructive interference that limits the detected signal magnitude. In contrast, the use of multiple-channel detection allows the pixels 60 to respectively detect subsets of optical modes of the interference light pattern 40 during each measurement period t, with the accompanying advantage of boosting light collection efficiency, maximizing the number of photons collected without destructive averaging, and leading to higher SNR.

Because the physiologically-encoded signal light 36 includes many optical pathlengths that correspond to the depths at which the sample light portions 34a-34d of the sample light 34 traverse the brain 12 (see FIG. 2), the resulting interference light pattern 40 is a high-frequency bandwidth signal that would typically require a tremendous amount of processing power and power consumption to extract the relevant signal from the interference light pattern 40 over many independent channels if digitally performed. However, in order to achieve a large number of parallel channels with a relatively small processing power small power consumption (e.g., less than 100 s of mW), the multi-channel optical detector chip 24 takes advantage of the fact that changes in physiologically-dependent optical signals typically occur at much slower speeds (e.g., in the KHz range) than the oscillation frequency components in the raw physiologically-encoded signal light 36 (e.g., in the MHz range).

Significant to the present inventions, the optical measurement system 10 is capable of suppressing the DC offset (i.e., the DC component) in the interference light pattern 38, including any fluctuations in the DC offset, while still using a single optical combiner 46 to generate the interference light pattern 38. In particular, instead of pairing corresponding optical detectors of a pair of optical detector arrays, the optical measurement system 10 pairs optical detectors 60 in a single detector array (which in this case is incorporated into the optical detector chip 24) that receives the interference light pattern 40 from the single optical beam combiner 46.

Figure 9:
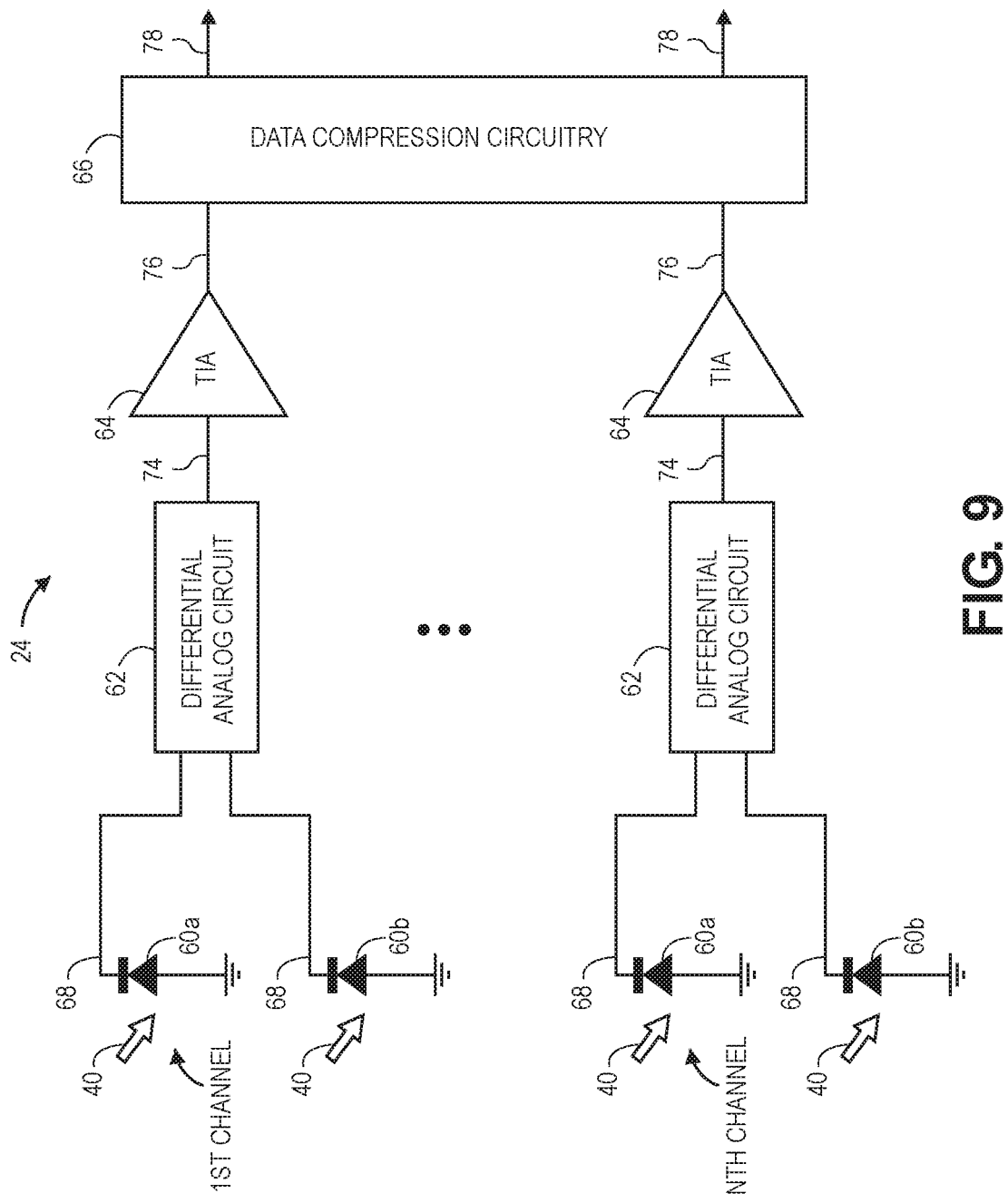
FIG. 9 is a block diagram of electronic componentry of one embodiment of an optical detector chip used in the optical measurement system of FIG. 2.
Figure 10:
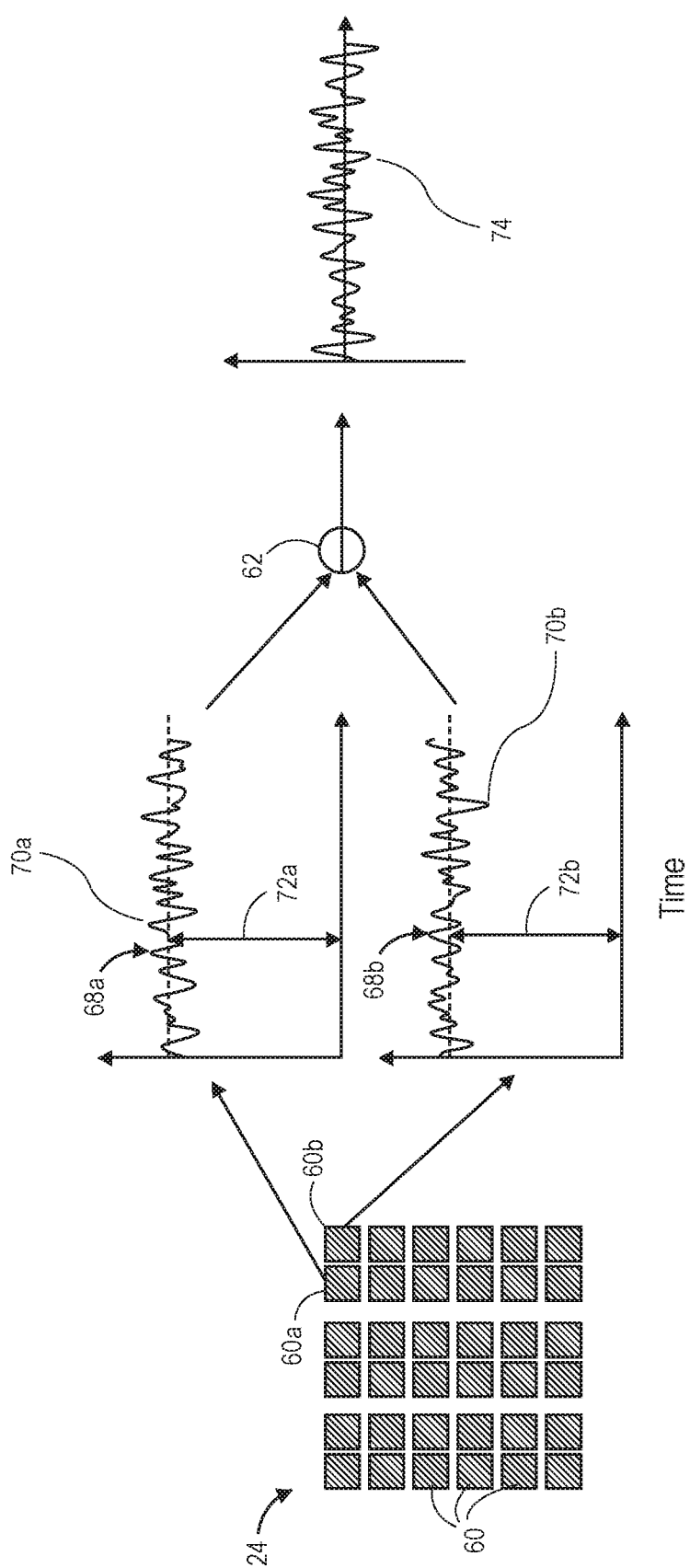
FIG. 10 is a plan view illustrating the signals internally generated by the optical detector chip of FIG. 9.

To this end, and with reference to FIGS. 9 and 10, the optical detectors 60 (shown as photodiodes, although other types of optical detectors are contemplated by the invention) are respectively configured for detecting the subsets of optical modes of the interference light pattern 40, as described above, and thus the physiologically-encoded signal light 36, and outputting a plurality of analog signals 68 corresponding to the subsets of optical modes of the interference light pattern 40.

It should be appreciated that, although it is preferred that each subset of optical modes of the interference light pattern 40 detected by an optical detector 60 comprise multiple spatially adjacent optical modes, each subset of optical modes of the interference light pattern 40 detected by an optical detector 60 may comprise a single (i.e., only one) optical mode. In any event, each optical detector 60 should be sized to detect at least one optical mode of the interference light pattern 40. Each subset of optical modes of the interference light pattern 40 detected by the respective optical detector 64 has a large DC component and a very small, high frequency, AC component.

Figure 1:
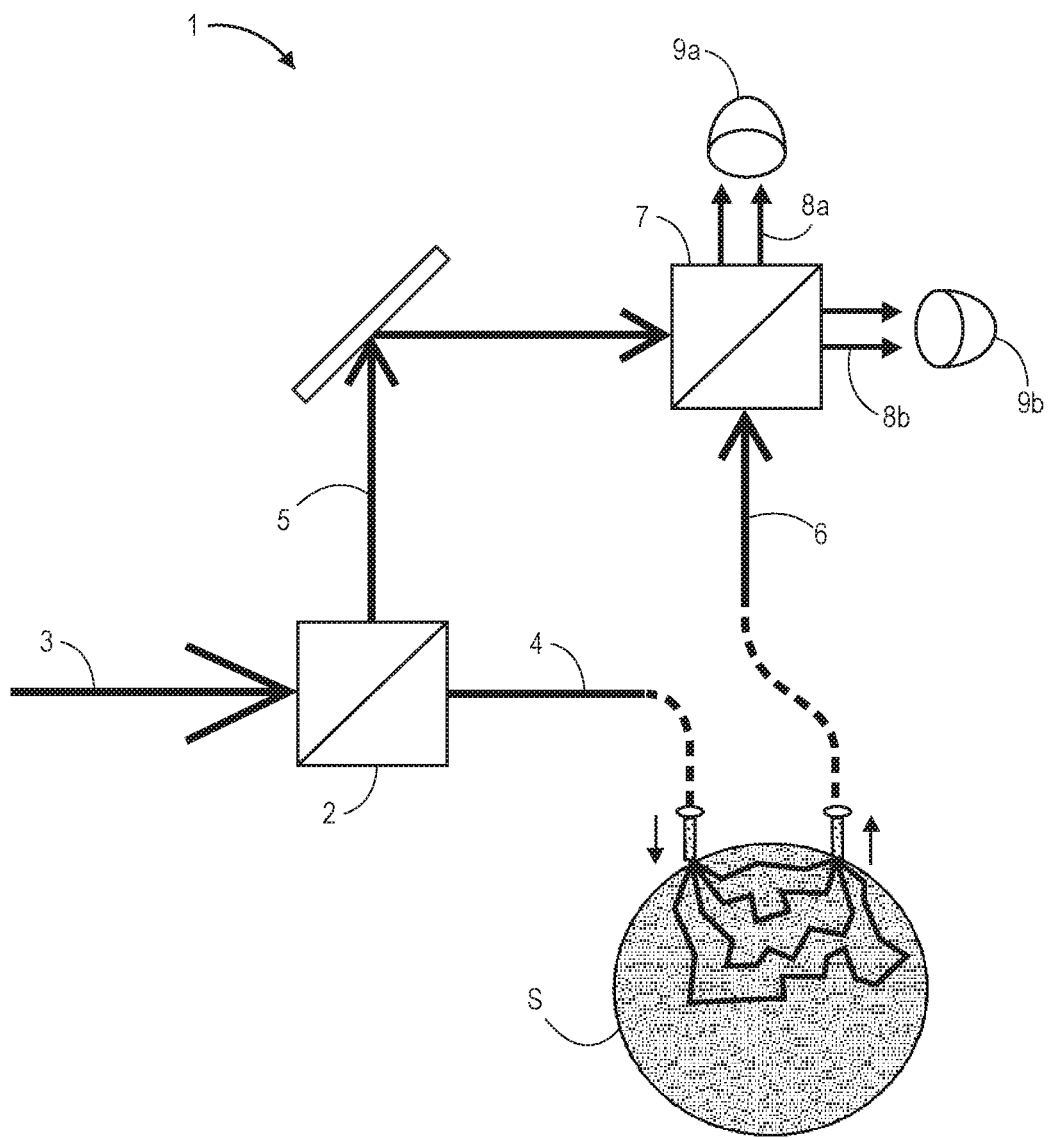
FIG. 1 is a block diagram of a prior art optical measurement system that utilizes a conventional fully balanced detection arrangement.

Significantly, the optical detectors 60 are arranged in pairs of neighboring optical detectors 60a, 60b, one for each channel N. In contrast to a conventional fully balanced detection arrangement, where each optical detector pair detects a split optical mode of the interference light (i.e., the same optical mode of the interference light is detected by the optical detector pair), as shown in FIG. 1, the optical detector chip 24 employs a partially balanced detection arrangement in which each optical detector pair 60a, 60b of the optical detector chip 24 detects two different optical modes of the interference light pattern 40, and outputs analog signals 68a, 68b respectively comprising AC components 70a, 70b and DC components (or offset) 72a, 72b of the two optical modes of the interference light pattern 40. In this case, the AC components 70 of the analog signals 68a, 68b corresponding to the two optical modes of the interference light pattern 40 detected at each optical detector pair 60a, 60b are uncorrelated, whereas, due to the proximity of the pair of optical detectors 60a, 60b, the DC offsets 72a, 72b of the of the analog signals 68a, 68b corresponding to the pair of optical modes of the interference light pattern 40 detected at each optical detector pair 60a, 60b are virtually identical.

The optical detector chip 24 further comprises a plurality of differential analog circuits 62 (only one shown in FIG. 10) configured for respectively subtracting pairs of the analog signals 68a, 68b from each other, and outputting a plurality of differential analog signals 74. By computing the difference between the pair analog signals 68a, 68b corresponding to each pair of optical modes of the interference light pattern 40, the DC offsets 72a, 72b are virtually cancelled, whereas the intensity of the pair analog signals 68a, 68b remains and increases by a square root of two due to random summation. In particular, each pair of optical detectors 60a, 60b share the same reference light intensity, since the intensity of the reference light 36 can be assumed to be uniform over a short distance. In contrast, the signal light 34, which develops optical speckles, has uncorrelated intensity and phase at each pair of optical detectors 60a, 60b, because of random interference after scattering.

In this case, the intensity of the interference light pattern 38 detected by each optical detector pair 60a, 60b can be given as:

$$I_A = I_{SA} + I_R + 2\sqrt{I_{SA}I_R}\cos(\Delta\omega t + \Delta\theta_A); \text{ and} \qquad [7a]$$

$$I_B = I_{SB} + I_R + 2\sqrt{I_{SB}I_R}\cos(\Delta\omega t + \Delta\theta_B), \qquad [7b]$$

where $I_{SA}$ and $I_{SB}$ are the intensities of the signal light 34 respectively detected by the optical detector pair 60a, 60b, $I_R$ is the intensity of the reference light 36, and $\Delta\theta_A$ and $\Delta\theta_B$ are the phases differences between the signal light 34 and reference light 36 (i.e., the AC interference term) respectively detected by the optical detector pair 60a, 60b. Because the signal light intensities $I_{SA}$ and $I_{SB}$ are much weaker than the reference light intensity $I_R$, the intensity of the interference light pattern 38 detected by each optical detector pair 60a, 60b given by equations [7a] and [7b] can be respectively approximated as:

$$I_A \approx I_R + 2\sqrt{I_{SA}I_R}\cos(\Delta\omega t + \Delta\theta_A); \text{ and} \quad [8a]$$

$$I_B \approx I_R + 2\sqrt{I_{SB}I_R}\cos(\Delta\omega t + \Delta\theta_B). \quad [8b]$$

Because the reference light intensity $I_R$ is essentially uniform over the optical detectors 60a, 60b, a differential operation on the interference light pattern intensities $I_A$ and $I_B$ detected by the optical detector pair 60a, 60b will cancel the reference light intensities $I_R$ in the resulting differential analog signal 74. However, because the phase 20 differences $\Delta\theta_A$ and $\Delta\theta_B$ in the AC interference terms (i.e. between the signal light 34 and reference light 36) of equations [8a] and [8b] are not uniformly distributed over the optical detectors 60a, 60b, a differential operation on the interference light pattern intensities $I_A$ and $I_B$ detected by the optical detector pair 60a, 60b will not cancel the AC interference terms in the resulting differential analog signal 74.

The root mean square (RMS) of the differential analog signal 74 can be given as:

$$RMS(I_A - I_B) = \sqrt{(I_A - I_B)^2} = $$
$$\sqrt{[2\sqrt{I_{SA}I_R}\cos(\Delta\omega t + \Delta\theta_A) - 2\sqrt{I_{SB}I_R}\cos(\Delta\omega t + \Delta\theta_B)]^2} = $$
$$\sqrt{2I_SI_R + 2I_SI_R} = 2\sqrt{I_SI_R}. \quad [9]$$

As can be appreciated by equation [1] (unbalanced detection arrangement), equation [5] (fully balanced detection arrangement), and equation [9](partially balanced detection arrangement), the RMS of the differential analog signal 74 for partially balanced detection is $\sqrt{2}$ higher than that of unbalanced detection, but 2 lower than that of fully balanced detection. However, because partially balanced detection arrangement enables the optical detector chip 24 to independently detect many optical modes of the signal light 34, the overall RMS of the optical detector chip 24 is increased by the square root of the number N of channels in the optical detector chip 24, and thus, can be considered to be much more sensitive and have a much higher data throughput than a fully balanced detection arrangement that can only detect a single optical mode of signal light.

It should be appreciated that although the pair of optical detectors 60a, 60b are illustrated as being immediately adjacent to each other, the pair of optical detectors 60a, 60b can be spaced apart from each other anywhere on the optical detector chip 24 within reasonable limitations, and thus, need not be immediately neighboring to each other. Preferably, the spacing between the pair of optical detectors 60a, 60b is such that the reference signal intensity $I_R$ does not substantially vary at the pair of detectors 60a, 60b, such that the DC offset terms 72a, 72b (i.e., the approximated reference light intensities $I_R$) in equations [8a] and [8b]) are substantially cancelled. It is preferred that more than 90 percent, and more preferably more than 99 percent, of the DC offset terms be cancelled (i.e., less than 10 percent, and more preferably less than 1 percent, of any DC offset term in the differential analog signal 74 relative to the greatest DC offset term between equations [8a] and [8b] remains in the differential signal). It is contemplated that the center-to-center spacing between the pair of detectors 60a, 60b should be less than one millimeter, and preferably, less than one hundred microns, in order to achieve this result.

Figure 11A:
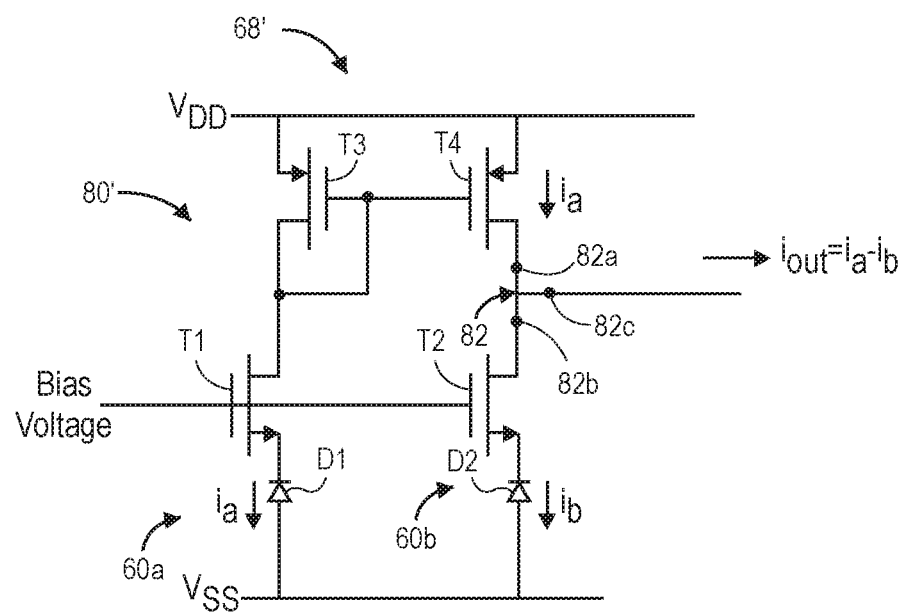
FIG. 11A is a schematic diagram illustrating one embodiment of a differential analog circuit used in the optical detector chip of FIG. 9.
Figure 11B:
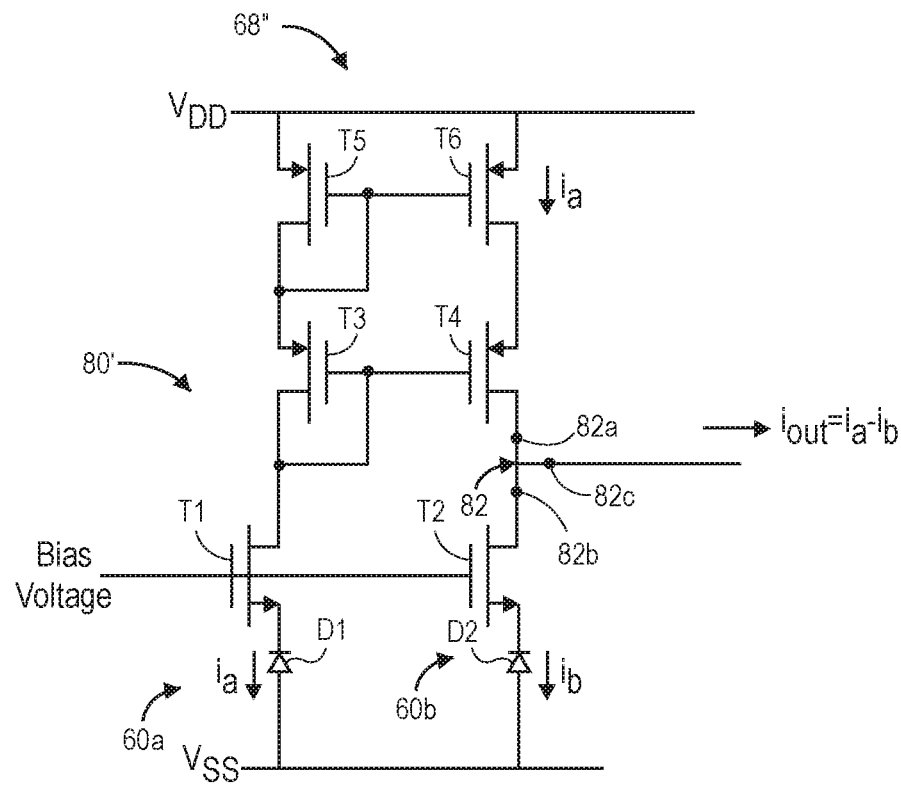
FIG. 11B is a schematic diagram illustrating another embodiment of a differential analog circuit used in the optical detector chip of FIG. 9.

Referring now to FIGS. 11A and 11B, each differential analog circuit 62 uses a current mirror arrangement that subtracts the pairs of the analog signals 68a, 68b from each other, and outputs the differential analog signals 74.

For example, one embodiment of a differential analog circuit 62', illustrated in FIG. 11A, comprises a plurality of single-stage current mirrors 80' (only one shown for brevity) configured for subtracting the electrical currents $i_a$, $i_b$ of the analog signals 68a, 68b corresponding to the pair of optical modes of the interference light pattern 40 detected at each optical detector pair 60a, 60b to produce differential currents $i_{out}$ (i.e., the differential analog signals 70). In particular, each optical detector pair 60a, 60b can be represented as diodes D1, D2 and respective transistors M1, M2, which are biased with a DC voltage, for respectively generating the electrical currents $i_a$, $i_b$ of the analog signals 68a, 68b in response to receiving the pair of optical modes of the interference light pattern 40.

The current mirror 80' comprises transistors M3, M4 respectively connected in series with the transistors M1, M2 of the optical detector pair 60a, 60b. The transistor M3, which is coupled in series with the transistor M1, is configured for mirroring the electrical current $i_a$ flowing through the transistor M1 of the optical detector 60a onto the transistor M4, which is coupled in series with the transistor M2 through which the electrical current $i_b$ flows.

The differential analog circuit 62' further comprises a three-port junction 82 having a first port 82a coupled to the transistor M4 of the current mirror 80', a second port 82b coupled to the transistor M2 of the optical detector 60b, and a third port 82c coupled to processing circuitry (not shown). Thus, the mirrored electrical current $i_a$ flowing through the transistor M4 of the current mirror 80' enters the junction 82 via the first input port 80a, while the electrical current $i_b$ exits the junction 82 and flows through the transistor M2 of the optical detector 60b. As a result, in accordance with Kirchoff's Current Law (KCL), differential current $i_{out}$ equal to the electrical current $i_a$ generated by the optical detector 60a minus the electrical current $i_b$ generated by the optical detector 60b, exits the junction 82 via the third port 82c for further processing and digitization by the optical detector chip 24 (along with other differential currents $i_{out}$ output by the differential analog circuit 62'), and ultimately, for processing by the processor 30 to determine neural activity in the brain 12, as discussed in further detail below.

Another example, another embodiment of differential analog circuit 62", illustrated in FIG. 11B, comprises a plurality of multi-stage (only one shown for brevity) current mirrors 80" configured for subtracting the electrical currents $i_a$, $i_b$ of the analog signals 68a, 68b corresponding to the pair of optical modes of the interference light pattern 40 detected at each optical detector pair 60a, 60b to produce differential currents $i_{out}$ (i.e., the differential analog signals 70). The differential analog circuit 62" differs from the differential analog circuit 62" illustrated in FIG. 11A in that each current mirror 80" has multiple stages of transistors (in this case, two stages), and thus, will more accurately mirror the electrical current $i_a$ through the transistor M1 of the optical detector 60a.

In particular, the current mirror 80" comprises transistors M3, M5 connected in series with the transistor M1 of the optical detector 60a, and transistors M4, M6 connected in series with the transistor M2 of the optical detector 60b. The transistors M3, M5, which are coupled in series with the transistor M1, is configured for mirroring the electrical current $i_a$ flowing through the transistor M1 of the optical detector 60a onto the transistors M4, M6, which are coupled in series with the transistor M2 through which the electrical current $i_b$ flows.

In the same manner described above in the differential analog circuit 62' of FIG. 11A, the mirrored electrical current $i_a$ flowing through the transistors M4, M6 of the current mirror 80" enters the junction 82 via the first input port 80a, while the electrical current $i_b$ exits the junction 82 and flows through the transistor M2 of the optical detector 60b. The differential current $i_{out}$, equal to the electrical current $i_a$ generated by the optical detector 60a minus the electrical current $i_b$ generated by the optical detector 60b, exits the junction 82 via the third port 82c for further processing and digitization by the optical detector chip 24 (along with other differential currents $i_{out}$ output by the differential analog circuit 62"), and ultimately, for processing by the processor 30 to determine neural activity in the brain 12, as discussed in further detail below.

The multi-channel optical detector chip 24 optionally performs high-frequency bandwidth processing steps of the physiologically-encoded signal light 36 for all of the channels to extract this slow time-varying information from the physiologically-encoded signal light 36 first, in effect compressing the high-bandwidth, information poor, signal light 36 into low-bandwidth, information rich, data with minimal power consumption. For example, if there are 1000 optical pathlengths (depths) of interest (although in practice, the number of optical pathlengths requires will be much less, e.g., 3 or 4), the bandwidth of the resulting low-bandwidth information will be approximately 1000 times less than the bandwidth of the raw interference light pattern 40.

This low-bandwidth information for all of the channels can then be digitized for further processing by the processor 30 to determine the presence and depth of a change in a physiologically-dependent optical signal (e.g., a fast-optical signal or hemodynamic changes), and thus the neural activity, within the brain 12. To facilitate data compression, the multi-channel optical detector chip 24 may also sequentially select each oscillation frequency component (e.g., oscillation frequency components f1-f4 illustrated in FIG. 7A), such that the processor 30 may analyze one optical pathlength (depth) (e.g., optical pathlengths L1-L4 in FIG. 7B) at a time. For example, if the number of channels is equal to 1000, and the optical pathlengths to be analyzed is 50, the rate of the digital information output by the optical chip 24 may be approximately 400 Mbit/sec, assuming 1000 frames of second and an 8-bit data value.

To this end, and with reference back to FIG. 9, the multi-channel optical detector chip 24 further comprises a plurality of amplifiers 64 (e.g., transimpedance amplifiers (TIAs)) respectively coupled to the outputs of the differential analog circuits 64 for amplifying the differential analog signals 74 and outputting amplified differential analog signals 76, and optional data compression circuitry 66 respectively coupled to the outputs of the amplifiers 64 for compressing the amplified differential analog signals 76 and outputting a plurality of low-bandwidth digital signals 78.

In one embodiment, the data compression circuitry 66 is configured for compressing the amplified differential analog signals 76 purely in the analog domain. In this case, the data compression circuitry 66 is configured for parallel processing the amplified differential analog signals 76 completely in the analog domain, and outputting the low-bandwidth digital signals 78, each having a frequency band less than the frequency band of the respective amplified differential analog signal 76. Further details discussing this data compression technique are set forth in U.S. Provisional patent application Ser. No. 62/834,504, entitled "Interferometric Parallel Detection Using Analog Data Compression," which is expressly incorporated herein by reference.

In another embodiment, the data compression circuitry 66 is configured for compressing the amplified differential analog signals 76 in both the analog domain and digital domain. In this case, the data compression circuitry 66 comprises analog compression circuitry (not shown) configured for parallel processing the plurality of differential analog signals 74 in the analog domain, and outputting a plurality of mid-bandwidth digital signals, each having a frequency band less than the frequency band of the respective amplified differential analog signal 76. The data compression circuitry 66 further comprises digital compression circuitry (not shown) configured for processing the plurality of mid-bandwidth digital signals over an i number of iterations, and outputting a plurality of low-bandwidth digital signals on the ith iteration, each low-bandwidth digital signal having a frequency band less than the frequency band of the respective mid-bandwidth digital signal. Further details discussing this data compression technique are set forth in U.S. Provisional patent application Ser. No. 62/855,405, entitled "Interferometric Parallel Detection Using Digital Rectification and Integration," which is expressly incorporated herein by reference.

The processor 30 may determine the presence and depth of a change in a physiologically-dependent optical signal (e.g., a fast-optical signal or hemodynamic changes), and thus the neural activity, within the brain 12, based on the low-bandwidth information (in the illustrated embodiment, the low-bandwidth digital signals 78) received from the multi-channel optical detector chip 24 using any one of a variety of techniques. In each technique, the processor 30 is configured for acquiring at least one array of extracted characteristics from the pixels 60 of the multi-channel optical detector chip 24 (i.e., over all of the channels) for the selected current optical pathlength of interest during at least one of the measurement periods t, reducing each array of extracted characteristics to a single characteristic (e.g., by computing a mean of array of characteristics), and determining the presence and depth (correlated to the selected optical pathlength L1-L4) of any change in the physiologically-dependent optical signal, at least partially, based on the reduced characteristic.

In one embodiment, the processor 30 determines the presence and depth of a change in a physiologically-dependent optical signal within the brain 12, e.g., by comparing the current TOF-intensity profile 54 of the physiologically-encoded signal light 36 (see FIG. 5B) (in this case, the reduced oscillation frequency component intensity value) with a user-specific baseline TOF-intensity profile (e.g., a previously acquired TOF-intensity profile 54) (in this case, a previously reduced oscillation frequency component intensity value).

Significantly, there is a strong correlation between the depth of penetration of photons of the sample light 34 within the brain 12 and the shape of the waveform of the detected physiologically-encoded signal light 36 in the time domain. That is, the TOF-intensity profile 54 can be correlated to spatial depth information (i.e., the tail end of the TOF-intensity profile 54 contains relatively deep information, whereas the front end of the TOF-intensity profile 54 contains relatively shallow information), and thus, the spatial depth of a change in a physiologically-dependent optical signal in the brain 12 may be determined. That is, it is known that the occurrence of the physiologically-dependent optical signal in the brain 12 will perturb the photons of the sample light 34 at the depth of the physiologically-dependent optical signal in the brain 12, thereby changing the intensity of the photons of the sample light 34 having an optical pathlength corresponding to that depth.

Figure 12A:
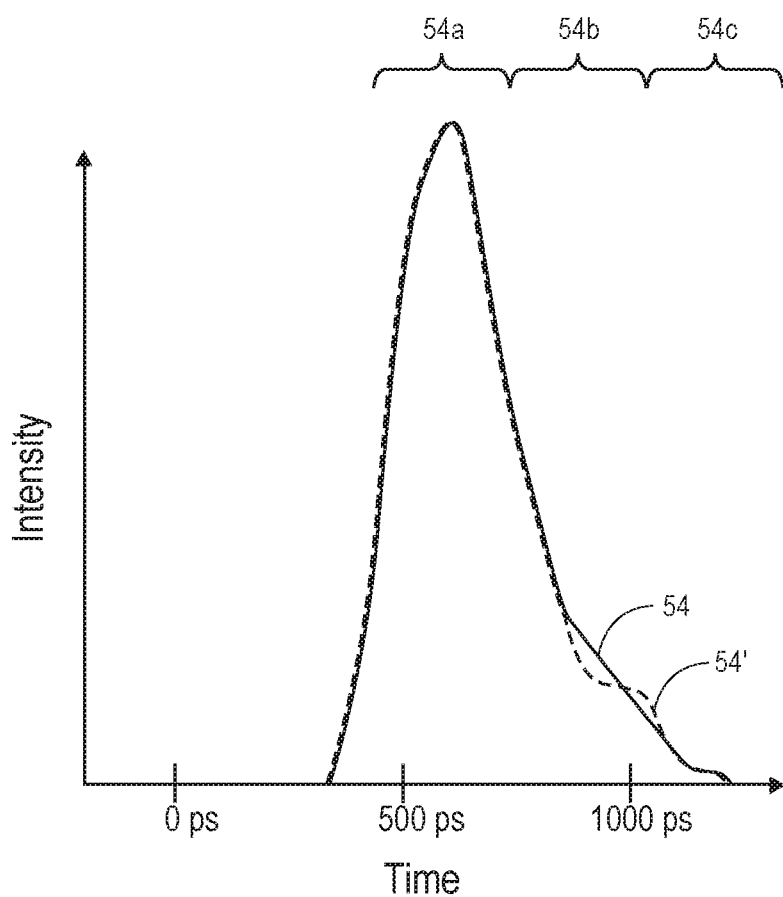
FIG. 12A is a timing diagram illustrating an exemplary TOF-intensity profile generated by the non-invasive optical detection system of FIG. 2.
Figure 12B:
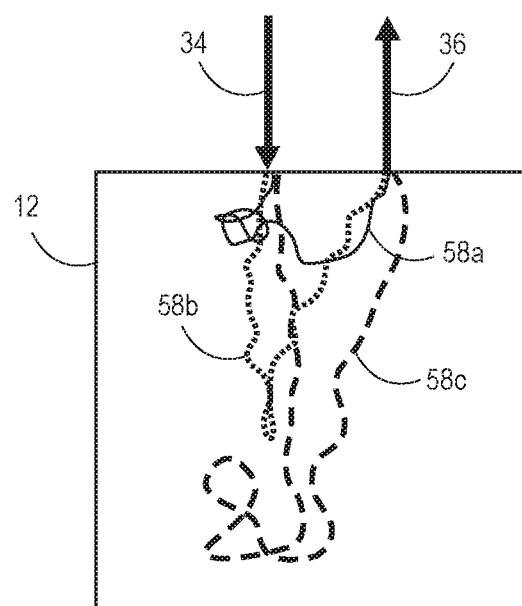
FIG. 12B is a plan view illustrating exemplary pathlengths of photons corresponding to different TOFs of the exemplary TOF-intensity profile of FIG. 12A.

For example, as further illustrated in FIGS. 12A and 12B, a relatively early time-bin 54a of the TOF-intensity profile 54 is weighted for photons that travel a relatively short distance along the detected optical path bundle 14 in the brain 12; that is, photons 58a that penetrate superficially into the brain 12; a later time-bin 54b of the TOF-intensity profile 54 is weighted for photons that travel a relatively medial distance along the detected optical path bundle 14 in the brain 12; that is, photons 58b that penetrate further into the brain 12; and an even later time-bin 54c of the TOF-intensity profile 54 is weighted for photons that travel a maximum distance along the detected optical path bundle 14 in the brain 12; that is, photons 58c that penetrate even further into the brain 12.

Thus, it can be appreciated that the TOF-intensity profile 54 of the detected signal light 36 contains intensity-optical pathlength information in which the spatial depth of a physiologically-encoded optical signal is encoded, and thus, a physiologically-encoded optical signal that changes at a certain depth in the brain 12 will cause a corresponding perturbation in the TOF-intensity profile 54. For example, as shown in FIG. 12A, there exists a perturbation between the baseline TOF-intensity profile 54 before a change in the physiologically-dependent optical signal, and a TOF-intensity profile 54' when the physiologically-dependent optical signal has changed. The change in the physiologically-dependent optical signal has a measurable perturbation in the TOF-intensity profile 54 in time-bins 54b and 54c, indicating a change in scattering or absorption in the photons in the mid-level or maximum depth in the brain 12, and thus, a change in the physiologically-dependent optical signal at this depth in the brain 12.

In another embodiment, the processor 30 determines the presence and depth of a change in a physiologically-dependent optical signal (e.g., a fast-optical signal or hemodynamic changes), and thus the neural activity, within the brain 12, e.g., by performing diffuse correlation spectroscopy (DCS) using an autocorrelation technique to determine the decorrelation speed of the time-lapsed complex field of the physiologically-encoded signal light 36 (in this case, the reduced oscillation frequency component intensity value).

Figure 13A:
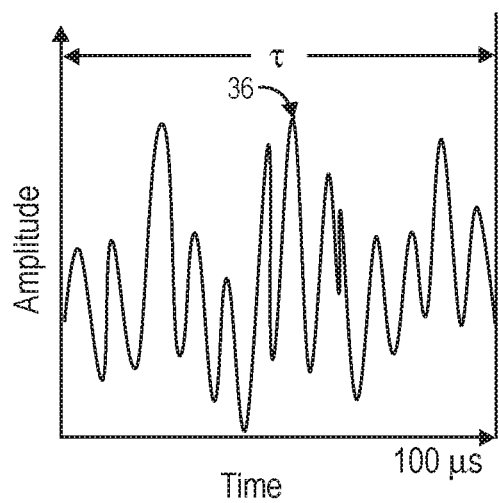
FIG. 13A is a timing diagram of an exemplary amplitude of physiologically-encoded signal light resulting in the delivery of sample light into an anatomical structure by the optical measurement system of FIG. 2.
Figure 13B:
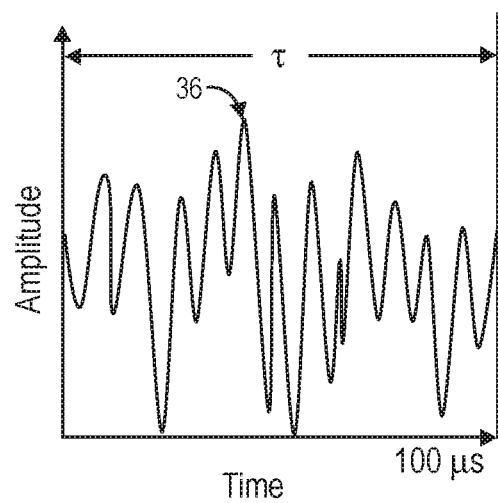
FIG. 13B is a timing diagram of an exemplary phase of physiologically-encoded signal light resulting in the delivery of sample light into an anatomical structure by the optical measurement system of FIG. 2.
Figure 13C:
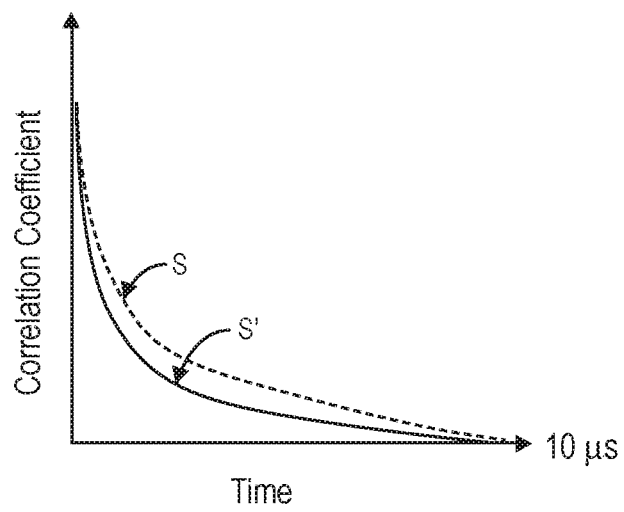
FIG. 13C is a timing diagram of exemplary decorrelation speeds of the physiologically-encoded signal light resulting in the delivery of sample light into an anatomical structure by the optical measurement system of FIG. 2.

One exemplary time-lapsed complex field of the physiologically-encoded signal light 36 in terms of intensity and phase is respectively plotted over a measurement period t of 100 µs, as illustrated in FIGS. 13A and 13B. As time lapses, the amplitude and phase of the physiologically-encoded signal light 36 fluctuates. The quicker the complex field of the physiologically-encoded signal light 36 fluctuates, the faster the physiologically-encoded signal light 36 decorrelates, and it is this decorrelation that the processor 30 measures in terms of decorrelation speed (i.e., the magnitude of decorrelation as a function of time). As illustrated in FIG. 13C, the decorrelation speed S indicates that the time-lapsed complex field of the physiologically-encoded signal light 36 decorrelates at an exponential rate, such that maximum correlation occurs at time=0, and complete decorrelation occurs at approximately time=10 µs.

Once the processor 30 obtains the decorrelation speed S of the time-lapsed complex field of the physiologically-encoded signal light 36, the processor 30 identifies a change in the physiologically-dependent optical signal in the brain 12, at least partially, by comparing the determined decorrelation speed of the complex field of the physiologically-encoded signal light 36 to a reference decorrelation speed. In one embodiment, the processor 30 identifies the physiologically-dependent optical signal, and thus the neural activity, at the depth in the brain 12, e.g., by comparing the current decorrelation speed S of the complex field of the physiologically-encoded signal light 36 with a predetermined baseline decorrelation speed or a user-specific baseline decorrelation speed S' (e.g., a previously determined decorrelation speed of the complex field of the physiologically-encoded signal light 36, as illustrated in FIG. 13C.

It can be appreciated that a fast-optical signal that occurs at the depth in the brain 12 of a user will increase the scattering of the physiologically-encoded signal light 36 at that depth, thereby increasing the decorrelation speed S of the physiologically-encoded signal light 36. Thus, a measurable change exists between the decorrelation speed S of the complex field of the physiologically-encoded signal light 36 in the presence of a change in the physiologically-dependent optical signal and the decorrelation speed S' of the complex field of the physiologically-encoded signal light 36 in the absence of a change in the physiologically-dependent optical signal, as illustrated in FIG. 13C.

Figure 14:
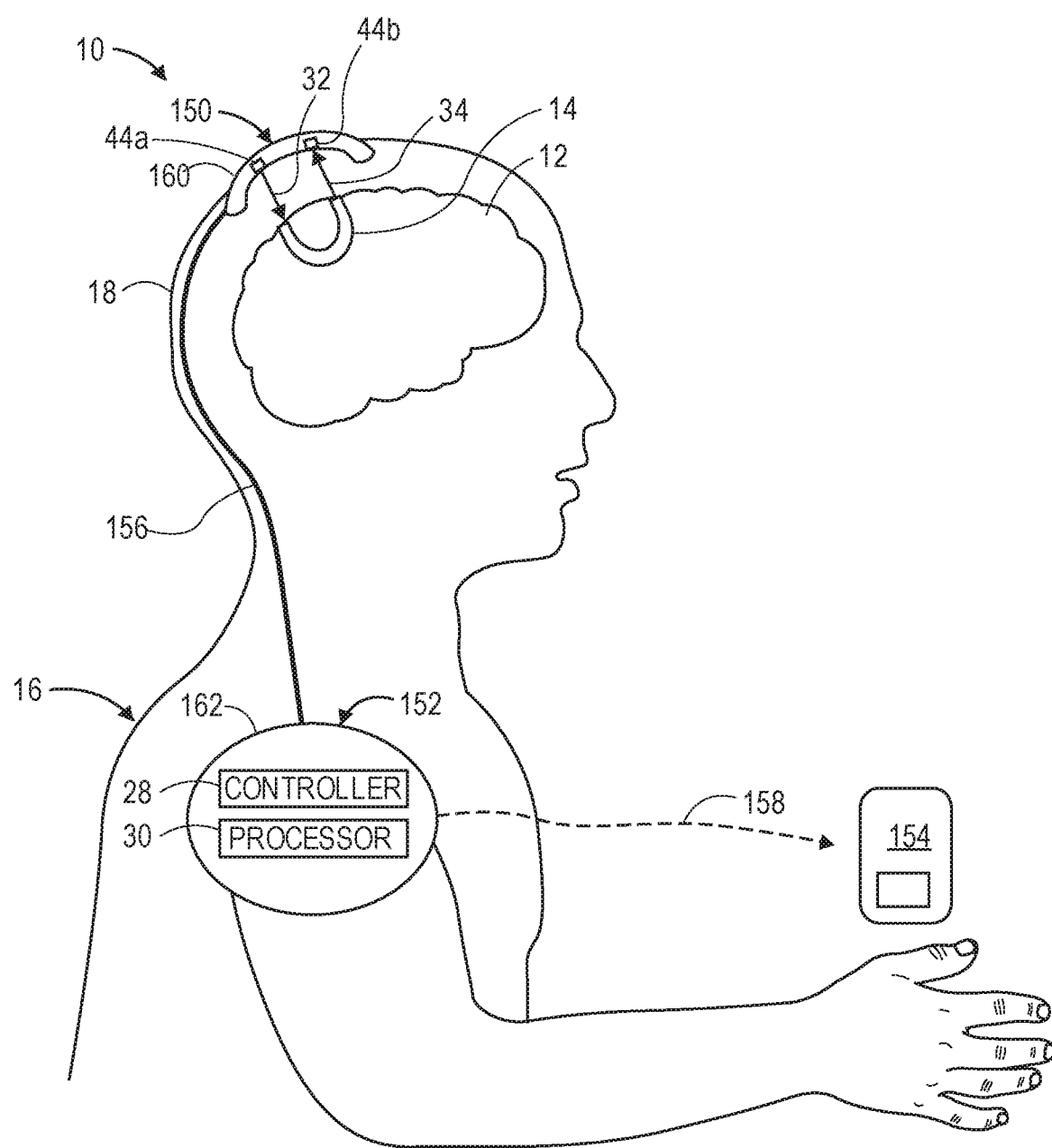
FIG. 14 is a plan view of a physical implementation of the non-invasive optical detection system of FIG. 1.

Referring now to FIG. 14, one physical implementation of the non-invasive optical detection system 10 for use in localizing a fast-optical signal in the brain 12 of a user 16 will be described. The non-invasive optical detection system 10 includes a wearable unit 150 that is configured for being applied to the user 16, and in this case, worn on the head 18 of the user 16; an auxiliary head-worn or non-head-worn unit 152 (e.g., worn on the neck, shoulders, chest, or arm) coupled to the wearable unit 150 via a wired connection 156 (e.g., electrical wires); and an optional remote processor 154 in communication with the user-wearable auxiliary unit 152 coupled via a wired connection 158 (e.g., electrical wires). Alternatively, the non-invasive optical detection system 10 may use a non-wired connection (e.g., wireless radio frequency (RF) signals (e.g., Bluetooth, Wifi, cellular, etc.) or optical links (e.g., fiber optic or infrared ($I_R$)) for providing power to or communicating between the respective wearable unit 150 and the auxiliary unit 152, and/or a wired connection between the auxiliary unit 152 and the remote processor 154.

The wearable unit 150 comprises the optical source 20, interferometer 22, optical detector chip 24, the output port 44a for emitting the sample light 34 generated by the optical source assembly 20 into the head 18 of the user 16, the input port 44b configured for receiving the physiologically-encoded signal light 36 from the head 18 of the user 16 and delivering it to the multi-channel optical detector chip 24 (illustrated in FIGS. 1 and 3), and a support structure 160 containing the optical source 20, interferometer 22, optical detector chip 24 (or optical detector chips 24), and ports 44a, 44b.

The auxiliary unit 152 comprises the controller 28 and the processor 30, and is analogous to the computing device 26 (illustrated in FIG. 4). The auxiliary unit 152 further comprises a housing 162 containing the controller 28 and processor 30. The controller 28 is configured for controlling the operational functions of the wearable unit 150, whereas the processor 30 is configured for processing the neural-encoded signal light 34 acquired by the wearable unit 150 to localize the fast-optical signal within the brain 12. The auxiliary unit 152 may additionally include a power supply (which if head-worn, may take the form of a rechargeable or non-chargeable battery), a control panel with input/output functions, a display, and memory. Alternatively, power may be provided to the auxiliary unit 152 wirelessly (e.g., by induction). The remote processor 154 may store data from previous sessions, and include a display screen.

Figure 15:
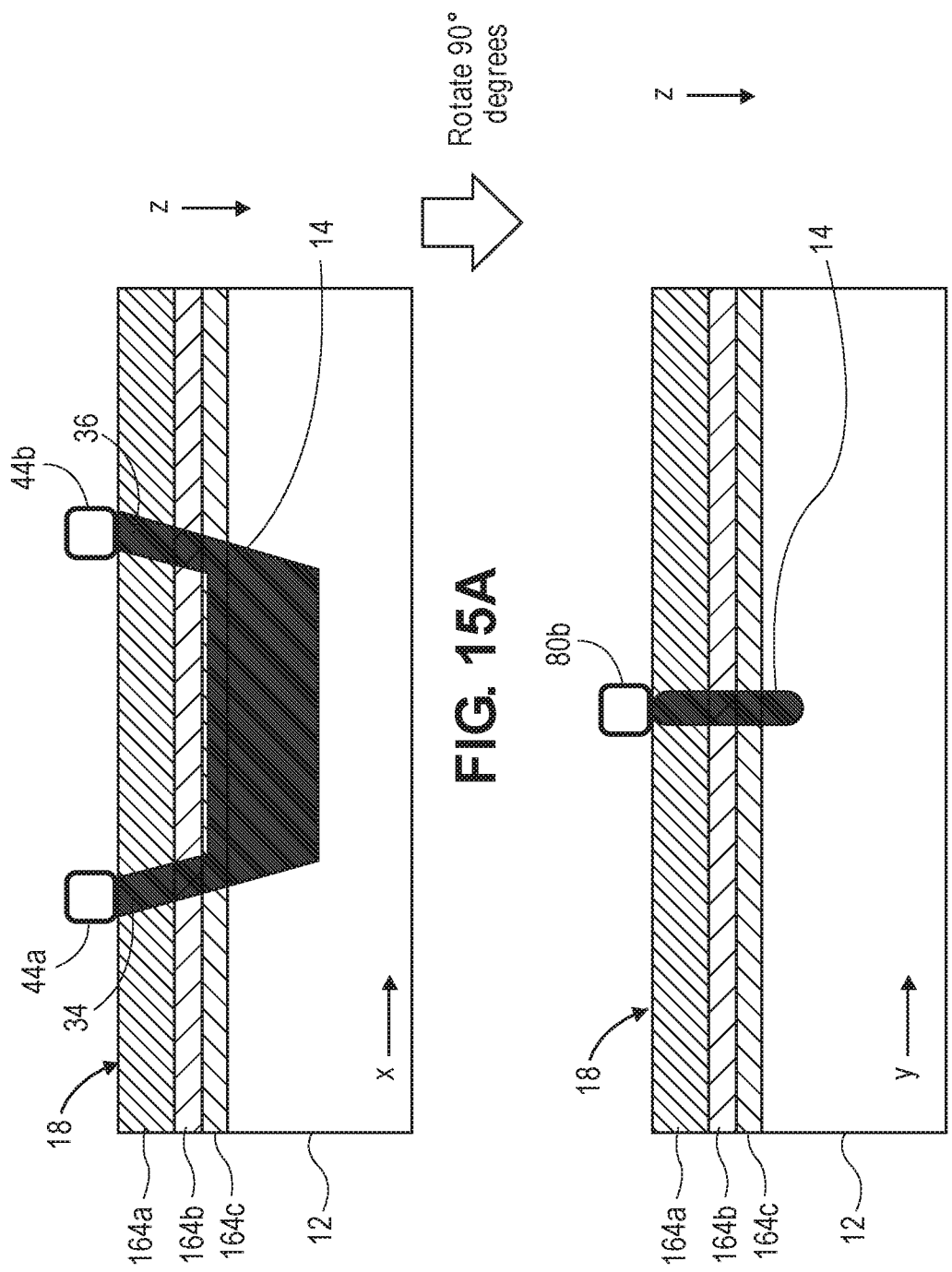
FIG. 15A is one profile view of one arrangement of the output port and input port of the wearable unit of FIG. 14, particularly illustrating the creation of a sample path in the head between the ports.
FIG. 15B is another profile view of the arrangement of the output port and input port of the wearable unit of FIG. 14.

As better illustrated in FIGS. 15A and 15B, the wearable unit 150 is configured for being placed adjacent to the head 18 of the user 16 and emitting the sample light 34 into the brain 12, where is scatters, resulting in the neural-encoded signal light 36 that exits the brain 12. In particular, the sample light 34 first passes through the scalp 164a, skull 164b, and cerebral spinal fluid (CSF) 164c along a relatively straight path, enters the brain 12, then exits in reverse fashion along a relatively straight path through the CSF 164c, skull 164b, and scalp 164a, thereby defining a banana-shaped optical path bundle 14. The wearable unit 150 may alternatively, by adding additional optical source-detector pairs, create multiple spatially separated detected optical path bundles 14 along which the light may propagate to enable x-y spatial localization of the fast-optical signal. For details discussing wearable units with multiple source-detector pairs are described in U.S. Provisional Patent Application Ser. No. 62/829,124, entitled "Modulation of Mental State of a User Using a Non-Invasive Brain Interface System and Method," which is expressly incorporated herein by reference.

Referring back to FIG. 14, the support structure 160 may be shaped, e.g., have a banana, headband or hat shape, or other shape adjustable to the head 18, such that the ports 44a, 44b are in close contact with the outer skin of the head 18, and in this case, the scalp of the user 16. In an alternative embodiment, optical fibers (not shown) may be respectively extended from the ports 44a, 44b, thereby freeing up the requirement that the ports 44a, 44b be disposed in close proximity to the surface of the head 18. In any event, an index matching fluid may be used to reduce reflection of the light generated by the wearable unit 150 from the outer skin of the scalp. An adhesive or belt (not shown) can be used to secure the support structure 160 to the head 18 of the user 16.

Figure 16:
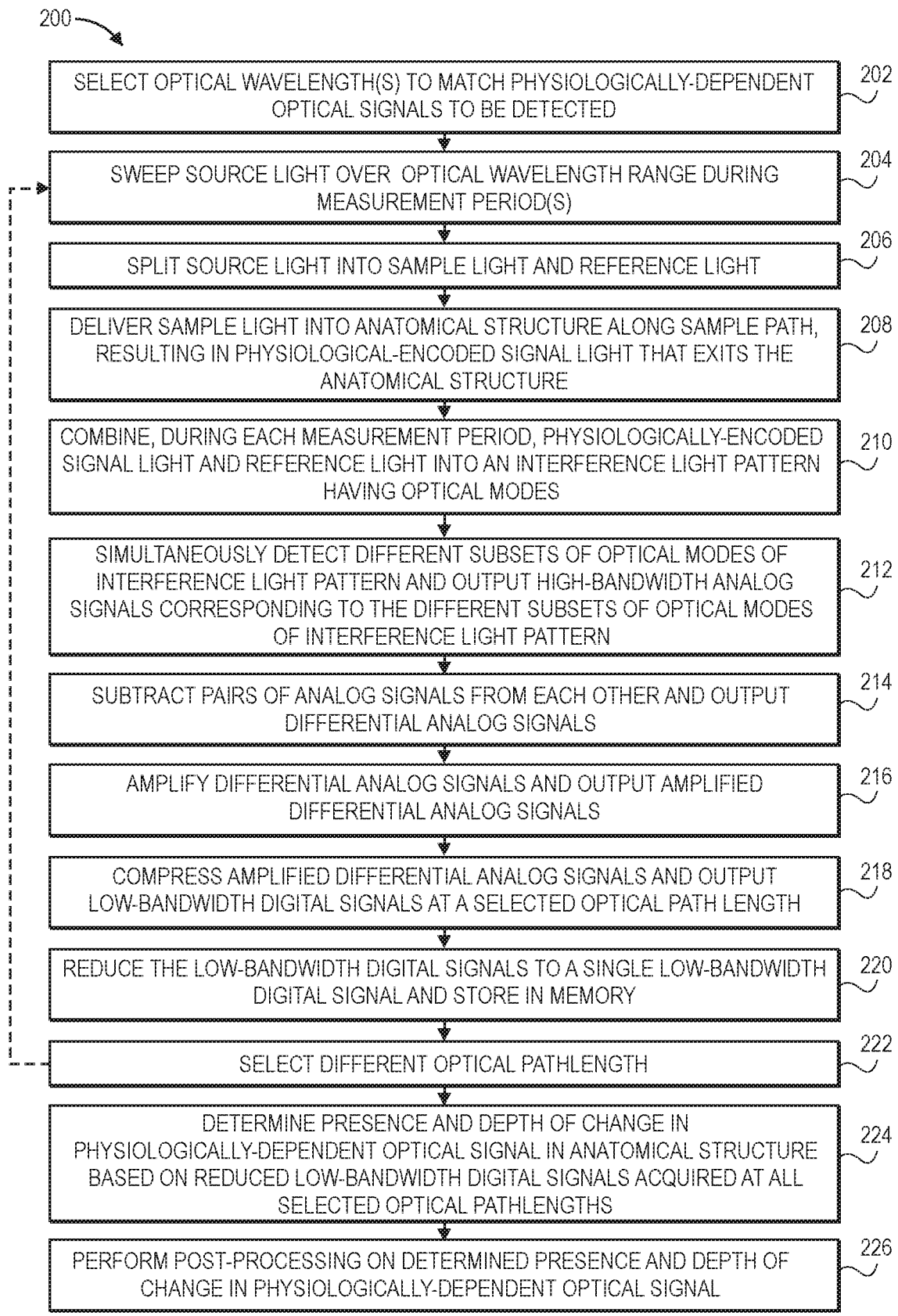
FIG. 16 is a flow diagram illustrating one method used by the non-invasive optical detection system of FIG. 2 to non-invasively determine the presence and depth of a physiologically-dependent optical signal within an anatomical structure.

Referring to FIG. 16, having described the structure and function of the non-invasive optical detection system 10, one particular method 200 performed by the non-invasive optical detection system 10 to non-invasively determine the depth of a change in a physiologically-dependent optical signal (e.g., a fast-optical signal or a hemodynamic change) in the anatomical structure 12 (in this case, the brain) will now be described.

First, the optical wavelength(s) of the source light 32 is selected to match the physiologically-dependent optical signal to be detected in the brain 12 (step 202). In the case where the physiologically-dependent optical signal is a fast-optical signal, the optical wavelength may be greater than 850 nm. In the case where the physiologically-dependent optical signal is blood oxygen concentration, the optical wavelength may be selected to be in the range of 650 nm to 750 nm.

Next, the controller 28 sends a control signal to the drive circuit of the optical source 20 to repeatedly sweep the source light 32 over the optical wavelength range 50 during one or more measurement periods t, with each measurement period t corresponding to a single optical wavelength range sweep 50 (step 204). As discussed above, each measurement period t is preferably equal to or less than the speckle decorrelation time of the brain 12, e.g., equal to or less than 100 microseconds, and preferably, equal to or less than 10 microseconds.

The interferometer 22 (e.g., via the optical beam splitter 44) splits the source light 32 into the sample light 34 and the reference light 38 (step 206). The interferometer 22 then delivers the sample light 34 into the brain 12 along a single detected optical path bundle 14, such that the sample light 34 is scattered by the brain 12, resulting in physiologically-encoded signal light 36 that exits the brain 12 (step 208), and combines, during each of the measurement period(s) t (i.e., each sweep of the optical wavelength sweep 50), the physiologically-encoded signal light 36 and the reference light 38 into an interference light pattern 40 having a plurality of optical modes, with each optical mode having a plurality of oscillation frequency components (collectively, a first frequency band) respectively corresponding to a plurality of different optical pathlengths (e.g., optical pathlengths L1-L4) (i.e., respectively encoded with a plurality of different depths in the brain 12) (step 210).

While the optical wavelength of the source light 32 is repeatedly varied over the selected optical wavelength range 50, the optical detection system 10 (via the optical detectors 60 of the multi-channel optical detector chip 24) simultaneously detects different subsets of the plurality of optical modes of the interference light pattern 40 (i.e., sampled across the optical wavelength range) during each of the measurement period(s) t, and outputs a plurality of analog signals 68 respectively corresponding to the different subsets of optical modes of the interference light pattern 40 (step 212).

The optical detection system 10 (via the differential analog circuits 62 of the multi-channel optical detector chip 24) respectively subtract pairs of the analog signals 68a, 68b from each other, and outputs a plurality of differential analog signals 74 (step 214). In effect, the DC components 72a, 72b of the respective analog signals 68a, 68b will have been removed, and thus, the differential analog signals 74 will essentially be purely AC analog signals. Preferably, subtracting the pairs of the analog signals 68a, 68b from each other cancels at least a portion of other DC components 72a, 72b in the respective pair of analog signals 68a, 68b, such that the respective differential analog signal 74 has a DC component that is less than ten percent, and more preferably less than one percent, of the average of the DC components 72a, 72b in the respective pair of analog signals 68a, 68b.

The optical detection system 10 (via the amplifiers 64 of the multi-channel optical detector chip 24) then amplifies the differential analog signals 74 and outputs amplified differential analog signals 76 (step 216). The optical detection system 10 (via the data compression circuitry 66 of the optical detector chip 24) then optionally compresses the amplified differential analog signals 76 and outputs a plurality of low-bandwidth digital signals 78, each having a frequency band less than a frequency band of the respective differential analog signal 74 (step 218).

In one method, the amplified differential analog signals 76 are compressed by parallel processing the differential analog signals 76 completely in the analog domain, and outputting the low-bandwidth digital signals 78. In another method, the amplified differential analog signals 76 are compressed by parallel processing the amplified differential analog signals 76 in the analog domain, and outputting a plurality of mid-bandwidth digital signals, each having a frequency band less than a frequency band of the respective differential analog signal 74, and then processing the mid-bandwidth digital signals over an i number of iterations in the digital domain, and outputting the low-bandwidth digital signals 78 on the ith iteration, each low-bandwidth digital signal 78 having a frequency band less than the frequency band of the respective mid-bandwidth digital signal.

For each plurality of low-bandwidth digital signals 78 acquired over the pairs of optical modes of the interference light pattern 40 (i.e., for each cycle of switch 76 closures), the processor 30 reduces the plurality of low-bandwidth digital signals 78 to a single digital signal (e.g., by computing a mean of the low-bandwidth digital signals 78) and stores the single digital signals in memory (not shown) (step 220).

In the case where the multi-channel optical detector chip 24 is capable of sequentially selecting each oscillation frequency component (e.g., oscillation frequency components f1-f4 illustrated in FIG. 7A), such that the processor 30 may analyze one optical pathlength (depth) (e.g., optical pathlengths L1-L4 in FIG. 7B) at a time, the controller 28 may optically or electrically select a different optical pathlength using, e.g., any one of the techniques set forth in U.S. patent application Ser. No. 16/266,818, entitled "Ultrasound Modulating Optical Tomography Using Reduced Laser Pulsed Duration," U.S. patent Ser. No. 16/299,067, entitled "Non-Invasive Optical Detection Systems and Methods in Highly Scattering Medium," and U.S. patent application Ser. No. 16/382,461, entitled "Non-Invasive Optical Detection System and Method," which are expressly incorporated herein by reference (step 222).

Steps 204-220 can then be repeated, where the source light 32 of the optical source 20 is swept over the range of optical wavelengths (step 204), the interferometer 22 generates the interference light pattern 40 (step 206-210), the multi-channel optical detector chip 24 the simultaneously detects subsets of optical modes of the interference light pattern 40 during each of the measurement period(s) t, outputs the analog signals 68 corresponding to the subsets of optical modes of the interference light pattern 40 (step 212), subtract pairs of the analog signals 68a, 68b from each other and outputs the differential analog signals 74 (step 214), amplifies the differential analog signals 74 and outputs amplified differential analog signals 76 (step 216), and optionally compresses the amplified differential analog signals 76 and outputs the low-bandwidth digital signals 78 at a selected optical path length (step 218), and the processor 30 reduces plurality of low-bandwidth digital signals 78 to a single low-bandwidth digital signal for storage in memory (step 220).

Once the low-bandwidth digital signals 78 have been acquired, reduced, and stored in memory for all of the selected optical pathlengths, the processor 30 then determines the presence and depth (correlated to the selected optical pathlength L1-L4) of any change in the physiologically-dependent optical signal, based on the reduced low-bandwidth digital signals for all of the selected optical pathlengths stored in the memory, e.g., by performing a TOF analysis (FIGS. 12A-12B) or a DCS analysis (FIGS. 13A-13C) (step 224).

In the case where multiple detected optical path bundles 14 through the brain 12 are created using complex source-detector arrangements (e.g., single-source multi-detector, multi-source single-detector, or multi-source multi-detector) to simultaneously create multiple detected optical path bundles 14 spatially separated from each other within the brain 12 in a single measurement period t, or by using a movable source-detector arrangement, the processor 30 may also determine the existence and location of a change in the physiologically-dependent optical signal in an x-y plane along the surface of the brain 12, such that a three-dimensional location of the change in the physiologically-dependent optical signal within the brain 12 is determined. The processor 30 then performs post-processing on the localized physiologically-dependent optical signal, e.g., determining the level and location of neural activity within the brain 12 (step 226).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

The invention claimed is:

1. A non-invasive optical detection system, comprising:
an optical source configured for generating source light during each of at least one measurement period;
an interferometer configured for splitting the source light into sample light, which propagates along a sample arm of the interferometer, and reference light, which propagates ong a reference arm of the interferometer, delivering the sample light into a sample, such that the sample light is scattered by the sample, resulting in signal light that exits the sample, and combining, during each of the at least one measurement period, the signal light and the reference light into an interference light pattern having a plurality of optical modes, each having a direct current (DC) component and at least one alternating current (AC) component;
an array of optical detectors configured for respectively detecting different subsets of the plurality of optical modes of the interference light pattern, and respectively outputting a plurality of analog signals representative of the plurality of optical modes of the interference light pattern;
differential analog circuitry configured for respectively subtracting pairs of the analog signals from each other, and respectively outputting a plurality of differential analog signals;
at least one processor configured for analyzing the sample based on the AC components of the plurality of differential analog signals.

2. The non-invasive optical detection system of claim 1, wherein each subset of optical modes of the interference light pattern comprises a single optical mode.

3. The non-invasive optical detection system of claim 1, wherein each subset of optical modes of the interference light pattern comprises multiple spatially adjacent optical modes.

4. The non-invasive optical detection system of claim 1, wherein the source light has a range of optical wavelengths during each of the at least one measurement period, such that at least one AC component of each optical mode of the interference light pattern comprises a plurality of oscillation frequency components respectively corresponding to a plurality of optical pathlengths extending through the sample, and wherein the at least one processor is configured for analyzing the sample at a plurality of depths respectively corresponding to the plurality of optical pathlengths.

5. The non-invasive optical detection system of claim 4, wherein the optical source is configured for sweeping the source light over the range of optical wavelengths during each of the at least one measurement period.

6. The non-invasive optical detection system of claim 1, wherein the sample is an anatomical structure.

7. The non-invasive optical detection system of claim 6, wherein the signal light is physiologically encoded with a physiologically-dependent optical signal in the anatomical structure, the plurality of analog signals are physiologically-encoded analog signals, and the at least one processor is configured for identifying a change in the physiologically-dependent optical signal in the anatomical structure based on the plurality of physiologically-encoded analog signals.

8. The non-invasive optical detection system of claim 7, wherein the anatomical structure is a brain, the physiologically-dependent optical signal is indicative of neural activity, and the at least processor is configured for identifying neural activity in the brain based on the identified change in the physiologically-dependent optical signal.

9. The non-invasive optical detection system of claim 8, wherein the physiologically-dependent optical signal is one of a fast-optical signal and a hemodynamic signal.

10. The non-invasive optical detection system of claim 1, wherein each of the at least one measurement period is equal to or less than a speckle decorrelation time of the sample.

11. The non-invasive optical detection system of claim 1, wherein the at least one processor is further configured for reducing the plurality of analog signals to a single signal, and the at least one processor is configured for analyzing the sample based on the single signal.

12. The non-invasive optical detection system of claim 1, further comprising an optical detector chip in which the plurality of optical detectors and the analog circuitry are integrated.

13. The non-invasive optical detection system of claim 1, further comprising data compression circuitry configured for respectively compressing the plurality of differential analog signals, and respectively outputting a plurality of low-bandwidth digital signals, each having a frequency band less than a frequency band of the respective differential analog signal, wherein the at least processor is configured for analyzing the sample based on the plurality of low-bandwidth digital signals.

14. The non-invasive optical detection system of claim 13, wherein the data compression circuity comprises analog compression circuitry configured for parallel processing the plurality of differential analog signals, and respectively outputting the plurality of low-bandwidth digital signals.

15. The non-invasive optical detection system of claim 13, wherein the data compression circuity comprises:

analog compression circuitry configured for parallel processing the plurality of differential analog signals, and respectively outputting a plurality of mid-bandwidth digital signals, each having a frequency band less than a frequency band of the respective differential analog signal; and digital compression circuitry configured for processing the plurality of mid-bandwidth digital signals over an N number of iterations, and respectively outputting the plurality of low-bandwidth digital signals on the Nth iteration, each low-bandwidth digital signal having a frequency band less than the frequency band of the respective mid-bandwidth digital signal.

16. The non-invasive optical detection system of claim 1, wherein each pair of analog signals corresponds to a pair of immediately neighboring ones of the plurality of optical detectors.

17. The non-invasive optical detection system of claim 1, wherein each pair of analog signals corresponds to a respective pair of optical detectors that has a center-to-center spacing less than one millimeter.

18. The non-invasive optical detection system of claim 17, wherein the respective pair of optical detectors has a center-to-center spacing less than one hundred microns.

19. The non-invasive optical detection system of claim 1, wherein subtracting the pairs of the analog signals from each other cancels at least a portion of the DC components in the respective pair of analog signals, such that the respective differential analog signal has a DC component that is less than ten percent of the average of the DC components in the respective pair of analog signals.

20. The non-invasive optical detection system of claim 19, wherein the respective differential analog signal has a DC component that is less than one percent of the average of the DC components in the respective pair of analog signals.

* * * * *